US009182408B2

(12) United States Patent
Mehtali

(10) Patent No.: US 9,182,408 B2
(45) Date of Patent: Nov. 10, 2015

(54) METHOD OF SCREENING BY USING CONFORMATION SENSITIVE PEPTIDES

(75) Inventor: Majid Mehtali, Coueron (FR)

(73) Assignee: VALNEVA, Lyons (FR)

( * ) Notice: Subject to any disclaimer, the term of this patent is extended or adjusted under 35 U.S.C. 154(b) by 892 days.

(21) Appl. No.: 11/662,873

(22) PCT Filed: Sep. 16, 2005

(86) PCT No.: PCT/IB2005/003323

§ 371 (c)(1), (2), (4) Date: Mar. 15, 2007

(87) PCT Pub. No.: WO2006/046134

PCT Pub. Date: May 4, 2006

(65) Prior Publication Data

US 2008/0076669 A1 Mar. 27, 2008

(30) Foreign Application Priority Data

Sep. 16, 2004 (EP) .................................... 04292224

(51) Int. Cl.

| | |
|---|---|
| ***C40B 40/10*** | (2006.01) |
| ***G01N 33/68*** | (2006.01) |
| ***C40B 20/04*** | (2006.01) |
| ***C07K 14/16*** | (2006.01) |
| ***G01N 33/566*** | (2006.01) |
| *C40B 40/02* | (2006.01) |

(52) U.S. Cl.

CPC .................................. *G01N 33/6845* (2013.01)

(58) Field of Classification Search

CPC ................ G01N 2333/70567; G01N 33/5008; G01N 33/5767; G01N 33/6845; G01N 2333/16

USPC ......................... 506/4, 14; 435/7.31; 530/350

See application file for complete search history.

(56) References Cited

U.S. PATENT DOCUMENTS

| | | | | |
|---|---|---|---|---|
| 5,071,773 | A | 12/1991 | Evans et al. | |
| 5,217,867 | A | 6/1993 | Evans et al. | |
| 5,298,429 | A | 3/1994 | Evans et al. | |
| 5,445,941 | A | 8/1995 | Yang | |
| 5,723,291 | A | 3/1998 | Kushner et al. | |
| 2003/0082827 | A1 | 5/2003 | Craig et al. | |
| 2003/0224390 | A1 * | 12/2003 | Fowlkes et al. | 435/6 |
| 2004/0043420 | A1 | 3/2004 | Fowlkes et al. | |

FOREIGN PATENT DOCUMENTS

| | | | |
|---|---|---|---|
| WO | WO 97/20952 | A1 | 6/1997 |
| WO | WO 97/31646 | * | 9/1997 |
| WO | WO 99/54728 | * | 10/1999 |
| WO | WO 99/54728 | A2 | 10/1999 |
| WO | WO 02/04956 | A2 | 1/2002 |

OTHER PUBLICATIONS

Vegeto et al. (The mechanism of RU486 antagonism is dependent on the conformation of the carboxy-terminal, 1992, Cell, vol. 69, pp. 703-713).*

Lan et al. (Direct interaction between—actinin and hepatitis C virus NS5B, 2003, FEBS Letters, vol. 554, pp. 289-294).*

Yang et al. (Cyclophilin A and FKBP12 interact with YY1 and alter its transcriptional activity, 1995, The Journal of Biological Chenistry, vol. 270, pp. 15187-15193).*

Sharma et al. (5'TG3' interacting factor interacts with Sin3A and represses AR-mediated transcription, 2001, Molecular Endocrinology, vol. 15, pp. 1918-1928).*

Suzuki et al. (Physical interaction between retinoic acid receptor and SP-1: mechanism for induction of urokinase by retinoic acid, 1999, Blood, vol. 93, pp. 4264-4276).*

Shiau et al., "Orphan nuclear receptors: From new ligand discovery technolgoes to novel signaling pathways," Current Opinion in Drug Discovery & Development, 2001, 4(5):575-590.

Gruenke et al., "New Insights into the Spring-Loaded Conformational Change of Influenza Virus Hemagglutinin," J. Virology, May 2002, 76(9), 4456-4466.

Karimova et al., "A bacterial two-hybrid system based on a reconstituted signal transduction pathway," Proc. Natl. Acad. Sci. USA, May 1998, 95, 5752-5756.

Kousteni et al., "Reversal of Bone Loss in Mice by Nongenotropic Signaling of Sex Steroids," Science, Oct. 25, 2002, 298, 843-846 and erratum.

Labonte et al., "Modulation of Hepatitis C Virus RNA-dependent RNA Polymerase Activity by Structure-based Site-directed Mutagenesis," J. Biol. Chem., Oct. 11, 2002, 277(41), 38838-38846.

Lo et al., "Interaction between Hepatitis C Virus Core Protein and E1 Envelope Protein," J. Virology, Aug. 1996, 70(8), 5177-5182.

McDonnell et al., "Analysis of Estrogen Receptor Function in vitro Reveals Three Distinct Classes of Antiestrogens," Molec. Endocrinol., 1995, 9, 659-669.

Miller et al., "Divorcing Estrogen's Bright and Dark Sides," Science, Oct. 25, 2002, 298, 723-724.

Norris et al., "Peptide Antagonists of the Human Estrogen Receptor," Science, Jul. 30, 1999, 285, 744-746.

Paige et al., "Estrogen receptor (ER) modulators each induce distince conformational changes in ER α and ER β," Proc. Natl. Acad. Sci. USA, Mar. 1999, 96, 3999-4004.

Rodriguez et al., "Gliotoxin: Inhibitor of Poliovirus RNA Synthesis That Blocks the Viral RNA Polymerase $3D^{pol}$," J. Virology, Apr. 1992, 66(4), 1971-1976.

Steinmetz et al., "Binding of Ligands and Activation of Transcription by Nuclear Receptors," Annu. Rev. Biophys. Biomol. Struc., 2001, 30, 329-359.

Tellinghuisen et al., "Interaction between hepatitis C virus proteins and host cell factors," Curr. Opin. Microbiol., 2002, 5, 419-427.

(Continued)

*Primary Examiner* — Sharmila G. Landau
*Assistant Examiner* — Shannon Janssen
(74) *Attorney, Agent, or Firm* — Foley & Lardner LLP

(57) ABSTRACT

The present invention relates to a screening technology that allows the isolation of peptides able to bind to target protein, the binding of which being sensitive to the protein conformation. The invention further provides a method to identify compounds that specifically and precisely modify the protein conformation and its biological activity. Finally, the invention relates to certain peptides obtained by the method of screening of the present invention and their use as therapeutic agent for the prevention or treatment of diseases.

22 Claims, 13 Drawing Sheets

(56) References Cited

OTHER PUBLICATIONS

Yamashita et al., "RNA-dependent RNA Polymerase Activity of the Soluble Recombinant Hepatitis C Virus NS5B Protein Truncated at the C-terminal Region," J. Biol. Chem., Jun. 19, 1998, 273(25), 15479-15486.
Zhu et al., "The role of the third β strand in gp120 conformation and neutralization sensitivity of the HIV-1 primary isolate DH012," PNAS, Dec. 18, 2001, 98(26), 15227-15232.
"What does the genotype of your strain mean?", http://www.dualsystems.com/knowledgebase/questions.php?questionid=50, retrieved Apr. 22, 2011.
"Commonly Used Auxotrophic Markers", Saccharomyces genome database (SGD), http://www.yeastgenome.org/alleletable.shtml, retrieved Apr. 22, 2011.
Brachmann et al., "Designer deletion strains derived from *Saccharomyces cerevisiae* S288C: a useful set of strains and plasmids for PCR-mediated gene disruption and other applications," *Yeast*, vol. 14, pp. 115-132, 1998.
Horovitz et al., "An accurate method for determination of receptor-ligand and enzyme-inhibitor disassociation constants from displacement curves," Proc. Natl. Acad. Sci. USA, vol. 84, pp. 6654-6658, Oct. 1987.
Van Criekinge et al., "Yeast Two-Hybrid: State of the Art," Biological Procedures Online, vol. 2, No. 1, pp. 1-38, Oct. 4, 1999.
Pakdel et al., "Human estrogen receptor mutants with altered estrogen and antiestrogen ligand discrimination," The Journal of Biological Chemistry, vol. 267, No. 5, pp. 3429-3437, Feb. 15, 1992.
Petit et al., "Two Complementary Bioassays for Screening the estrogenic potency of xenobiotics: recombinant yeast for trout estrogen receptor and trout hepatocyte cultures," Journal of Molecular Endocrinology, vol. 19, pp. 321-335, 1997.

* cited by examiner

| GROUP | SYSTEMATIC NAMES | FAMILY | SUBTYPE | TRIVIAL NAMES |
|---|---|---|---|---|
| I | NR1A1 | TR | α | c-erbA-1, THRA |
| | NR1A2 | | β | c-erbA-2, THRB |
| | NR1B1 | RAR | α | |
| | NR1B2 | | β | Hap, RARε |
| | NR1B3 | | γ | RARD |
| | NR1C1 | PPAR | α | |
| | NR1C2 | | β | PPARδ, NUC1, FAAR |
| | NR1C3 | | γ | |
| | NR1D1 | Rev-ErbA | α | EAR1, EAR1A |
| | NR1D2 | | β | RVR, HZF2, EAR1β, BD73 |
| | NR1F1 | ROR | α | RZRα |
| | NR1F2 | | β | RZRβ |
| | NR1F3 | | γ | TOR |
| | NR1H2 | LXR | β | UR, NER, OR-1, RIP15 |
| | NR1H3 | | α | DL1, LXR |
| | NR1H4 | FXR | | HRR1, RIP14, BAR |
| | NR1I1 | VDR | | |
| | NR1I2 | PXR | | SXR, PAR, ONR1 |
| | NR1I3 | CAR | | α: human; β: mouse, MB67 |
| II | NR2A1 | HNF-4 | α | TCF14 |
| | NR1A2 | | γ | |
| | NR2B1 | RXR | α | |
| | NR2B2 | | β | H-2RIIBP, RCoR-1 |
| | NR2B3 | | γ | |
| | NR2C1 | TR2 | α | TR2, R2-11 |
| | NR2C2 | | β | TR4, TAK1 |
| | NR2E1 | TLX | | TLL, XTLL |
| | NR2E3 | PNR | | |
| | NR2F1 | Coup-TF | α | EAR3, SVP44 |
| | NR2F2 | | β | ARP1, SVP40 |
| | NR2F6 | | γ | EAR2 |
| III | NR3A1 | ER | α | |
| | NR3A2 | | β | |
| | NR3B1 | ERR | α | ERR1 |
| | NR3B2 | | β | ERR2 |
| | NR3B3 | | γ | ERR3 |
| | NR3C1 | GR | | |
| | NR3C2 | MR | | |
| | NR3C3 | PR | | |
| | NR3C4 | AR | | |
| IV | NR4A1 | NGF1 | α | Nurr77, N10, R3, NAK1, TIS1 |
| | NR4A2 | | β | Nurr1, NOT, TINOR, RNR1, HZF3 |
| | NR4A3 | | γ | Nor1, MINOR, TEC, CHN |
| V | NR5A1 | FTZ-F1 | α | SF1 |
| | NR5A2 | | β | LRH1, FTF, PF, xFF1rA, xFFArB, FFLR, PHR |
| VI | NR6A1 | GCNF | | RTR |
| O | NR0B1 | DAX1 | | AhCH |
| | NR0B2 | SHP | | NR0B2 |

FIGURE 1

| Conformation-sensitive Peptide # | | AMINO-ACID SEQUENCE |
|---|---|---|
| 5-21 | (SEQ ID NO: 17) | S C C T Q H V C Y R P R A Y R |
| 9-23 | (SEQ ID NO: 18) | S I T T L F Y H A M F G F V P |
| 30-2 | (SEQ ID NO: 19) | F C T P I R M F Y R A P L W D L N K |

FIGURE 5

| Conformation-sensitive Peptide # | | AMINO-ACID SEQUENCE |
|---|---|---|
| I-B8 | (SEQ ID NO: 20) | M P A D I L F A N P Q C R I N |
| IC8 | (SEQ ID NO: 21) | A P F P V V Y W S D W C N Q Q |
| III-D2 | (SEQ ID NO: 22) | W V V Y A S L C F K A C Y F G L N K |
| II-F8 | (SEQ ID NO: 23) | A T L E W R L F T R F I T W G L I P L E |

FIGURE 7

METHOD OF SCREENING BY USING CONFORMATION SENSITIVE PEPTIDES

This application is a National Stage application of PCT/IB2005/003323, filed Sep. 16, 2005, which claims priority from European patent application EP 04292224.5, filed Sep. 16, 2004.

The present invention relates to the field of biology. More precisely, the invention provides a screening technology that allows the isolation of peptides able to bind to target protein, the binding of which being sensitive to the protein conformation. The invention further provides a method to identify compounds that specifically and precisely modify the protein conformation and its biological activity.

Many of the biological activities of proteins, either of animal, vegetal, bacterial or viral origin, are attributable to their tri-dimensional conformation and their ability to bind specifically to one or more binding partners (ligands), which may themselves be proteins, or other compounds, such as biomolecules or chemicals. The pharmacological value of such biologically active proteins lies in the ability of synthetic ligands to mimic or prevent the activities of natural protein-binding ligands.

When the binding partner of a protein is known, it is relatively straightforward to study how the interaction of the binding protein and its binding partner affects biological activity. Moreover, one may screen compounds for their ability to competitively inhibit the formation of the complex, or to dissociate an already formed complex. Such inhibitors are likely to affect the biological activity of the protein, at least if they can be delivered in vivo to the site of the interaction. However, most current known ligands are characterized by a poor protein specificity and tissue-selectivity, that can lead to serious side effects, as exemplified below with selective estrogen receptor modulator.

Unfortunately, the therapeutic potential of numerous proteins which are involved in physiological dysfunctions that can lead to human, animal or vegetal diseases and for which no natural ligands have yet been identified, remain practically untapped. There is therefore a crucial need in both, novel, more specific (eg. tissue-specific) protein-directed drugs that can modulate the activity of proteins. Such proteins, from cellular, bacterial or viral origin, may play a role in the treatment of pathologies either in humans, animals or plants.

Nuclear receptor proteins (NR) constitutes one of biologically active proteins with high pharmacological value. NR form an important superfamily of ligand-dependent transcription factors that specifically regulate the expression of target genes involved in the control of nearly every aspect of vertebrate development and adult physiology, such as embryonic development, cell differentiation, homeostasis, general metabolism, reproduction and behavior. The major importance of this protein family is illustrated by the demonstration that dysfunctions in nuclear receptor signaling have been implicated in numerous human disorders including diabetes, obesity, inflammation, cardiovascular diseases and cancer and by the already successful development of drugs targeting some of these receptors. For example, agonists as well as antagonists have been successfully developed for the Estrogen Receptor (ER) (eg. ESTRADIOL®, TAMOXIFEN®, RALOXIFEN®) or for the Peroxisome Proliferator-Activated Receptor gamma (PPARγ) (eg. ACTOS®, AVANDIA®) and are currently marketed for the treatments of post-menopausal disorders, breast cancer and type II diabetes, respectively. Given the key role of NRs in so many essential physiological functions and human diseases, this superfamily provides a large spectrum of potential targets for the development of new therapeutic drugs. The sequence of the human genome has revealed the existence of 48 nuclear receptors. The NR superfamily not only comprises receptors that bind small natural lipophilic signal molecules, but also includes a large number of receptors, the orphan receptors, for which no natural ligands have yet been identified. The existence of such orphan receptors offers the opportunity to identify new ligand-response systems and to develop new therapeutic agents. This is illustrated by the identification of natural and synthetic ligands for several nuclear receptors over the past years, which led to the discovery of unanticipated nuclear signaling pathways for retinoids, fatty acids, eicosanoids and steroids with important physiological and pharmacological ramifications.

NRs are transcriptional enhancer-binding proteins that regulate target gene expression by interacting as homo- or hetero-dimers with specific cis-acting DNA sequences (the response element RE) located upstream of their target genes. The NR activity is controlled through binding of natural lipophilic ligands, such as steroids, thyroid hormones and derivatives of vitamin A, D and fatty acids. Members of the nuclear receptor superfamily share several structural features including a central, highly conserved DNA binding domain (DBD) that targets the receptor to its cognate DNA response elements. The carboxy-terminal portion of the receptors includes the ligand binding domain (LBD), which interacts directly with the ligands. Embedded within the LBD is a ligand-dependent transcriptional activation function, AF-2, and in several instances a ligand-independent transcriptional silencing function. In addition, a ligand-independent activation function called AF-1 is located in the N-terminal region of most NRs, which acts in a cell- and promoter-specific context. The binding of the hormone to the receptor induces conformational changes and specific post-translational modifications (eg. phosphorylations) that control the receptor transcriptional properties and influence target gene expression. The conformational changes that accompany the transition between the unliganded and liganded forms of the nuclear hormone receptors affect dramatically their affinity for other proteins, such as the coactivator and corepressor complexes. It is ultimately the specific interactions of the nuclear receptors with defined cofactors that lead to the precise tissue-specific modulation of the target gene expression. Depending on which of the different nuclear receptors and cofactors are expressed in a cell, the biological activity of a given nuclear receptor and its ligand may change. Through this complex molecular interplay, nuclear receptors control the expression of a vast number of genes and metabolic pathways playing diverse roles in mammalian physiology, both in the normal and pathologic state. Therefore, in order to define the functional role of the hormone in a given tissue and to develop more efficient and safer drugs, one must better understand the subtle tissue-specific interactions between the receptor and its cofactors (coactivators and corepressors) and the nature of the conformational changes induced by ligand binding.

NRs are key regulators in major physiological processes that occur during embryonic development and in the adult. Dysfunction in NRs is thus often associated with serious disorders and most, if not all, members of this receptor superfamily constitute potential targets for therapeutic drug discovery. For example, Peroxisome proliferator-activated receptors (PPARs) play a crucial role in fatty acid metabolism, in inflammation control and in related diseases such as atherosclerosis. PPARγ is known to play a key role in adipocyte differentiation, cholesterol trafficking, glucose homeostasis and insulin sensitivity. In human, mutations in this receptor have been shown to be involved in disorders such as colon cancer, thyroid follicular carcinomas, type 2 diabetes, hypertension and obesity. Two PPARγ ligands, Actos® (Takeda) and Avandia® (GSK), have been successfully marketed for the management of type-II diabetes. This new class of oral drugs, the glitazones, exerts their antihyperglycemic effect by binding PPARγ which regulates the transcription of various insulin responsive genes necessary for the control of glucose and lipid metabolism. Sensitivity to insulin in adipose and muscle tissue is increased and hepatic gluconeogenesis is inhibited. The net effects include decreased blood glucose, insulin and triglyceride levels. Although the glitazones constitute an appealing new class of therapeutic agent for the treatment of diabetes, their use is also associated with side effects such as fluid retention, decreases in haemoglobin and haematocrit and a tendency to weight gain. In addition, Troglitazone (Depotox®), the first glitazone to reach the market, was recently withdrawn due to the elevated incidence of liver failures. While no such hepato-toxicities were reported for Actos® and Avandia®, the need for safer PPARγ drugs has stimulating several pharmaceutical and biotechnology companies active in the field to invest in the development of novel PPARγ partial agonists or antagonists. PPARγ appears also to exert a net protective action against atherosclerosis. As atherosclerosis is one of the most common causes of death in the industrialized world, the development of PPAR activators should decrease the incidence of cardiovascular diseases, by correcting metabolic disorders such as dyslipidemia, obesity and insulin resistance but also by direct action at the level of the vascular wall. Another NR target for anti-atherosclerotic drugs is Liver X Receptor alpha (LXRα). LXRα acts as a metabolic sensor for cellular cholesterol and oxysterol content and is involved in regulating cholesterol and triglyceride homeostasis. Increased oxysterol levels activate LXRα, which then in turn induces cholesterol removal out of peripheral cells, cholesterol transport to the liver, cholesterol excretion through production of bile acids, and inhibition of intestinal cholesterol absorption. Studies in animal models have also demonstrated that LXRα is involved in decreasing the risk of atherosclerosis. LXRα constitute therefore an attractive target for the prevention and/or reduction of atherosclerosis through induction of reverse cholesterol transport and stimulation of cholesterol catabolism. However, the clinical use of LXRα agonists is limited by their propensity to strongly increase triglyceride levels and to induce fatty acid synthesis, two risk factors for atherosclerosis. There is thus pressing need for drugs that selectively modulate the activities of LXRα. Besides PPARs and LXRα, several other NR targets, in particular among the orphan nuclear receptors, constitute attractive target for the development of therapies for human metabolic diseases (eg. LXRβ, FXR, LRH-1, SHP, HNF4, . . . ).

Nuclear receptors play also key roles in several human cancers such as breast, colon, liver or prostate cancers. For example, the human estrogen receptor alpha (ERα) is a well-established marker of breast cancer hormone sensitivity. The major natural targets of estrogens in females are the mammary glands and uterus, but estrogens are also essential in both males and females in maintenance of bone, brain, the cardiovascular system and the urogenital tract. Dysfunction in ERα signalling was linked to several human disorders such as hypofertility, breast cancer, cardiovascular diseases and osteoporosis. Pure antagonists and selective estrogen receptor modulators (SERMs) have been developed and are currently marketed for the treatment of breast cancer. While such drugs (eg. Tamoxifen®) have shown significant clinical benefit in treating and preventing breast cancer, their drawbacks have included an elevated incidence of uterine cancer and cognition deficits, stimulating active research for the development of novel generations SERMs with reduced side effects. Such a SERM, Evista®, (Raloxifene) was shown to reduce bone resorption, decrease overall bone turnover and increase bone mineral density and was approved for the prevention or treatment of osteoporosis in postmenopausal women. Results from osteoporosis prevention studies also demonstrate that Raloxifene acts as an antagonist in breast and uterus and thus may reduce the incidence of estrogen receptor-positive breast cancers and decrease the risk of endometrial cancer. However, about one-third of patients with ERα-positive breast tumors will not respond favorably to administration of anti-estrogens. The reason of this failure remains mostly unknown, but a better understanding of this resistance would open the door to the development of novel anti-estrogens. Retinoic acid receptor alpha (RARα) was also shown to be implicated in human cancers. Its natural ligands, retinoids, have been shown to exert pleiotropic effects. In human, a chromosomal translocation has been found in acute promyelocytic leukemia between RARα and PML genes. The treatment of this cancer is, at the molecular level, not well understood and exhibits important secondary effects. Development of novel small molecules is thus also of major therapeutic importance.

The important pharmacological value of nuclear receptors lies therefore in the ability of synthetic ligands to mimic or prevent the activities of natural ligands. Most current ligands are characterized by a poor receptor specificity and tissue-selectivity, leading to serious side effects. In addition, the therapeutic potential of most nuclear receptors, the so-called orphan nuclear receptors for which no ligands have yet been identified, remain practically untapped. There is a crucial need in both novel more specific nuclear receptor drugs and in drugs that can modulate the activity of nuclear receptors, which play a role in human pathologies.

Viral proteins constitute another group of biologically active proteins with high pharmacological value. Drugs to deal with viral infections are a field of medicine that has been traditionally weak. However since the 1980s, the full genetic sequences of viruses began to be available to researchers, and they began to learn how viruses worked in detail, and to envision what kind of molecules were needed to jam their machinery. The general idea behind modern antiviral drug design is to identify viral proteins, or parts of proteins, that can be disabled. The targets should also be common across many strains of a virus, or even among different species of virus in the same family, so a single drug will have broad effectiveness. Dozens of "antiviral" treatments are now available, and a lot are currently under development. Most of the antivirals now available are designed to help deal with HIV, herpes virus, the hepatitis B and C viruses and influenza viruses.

Viral life cycles vary in their precise details depending on the species of virus, but they all share a general pattern:

Attachment to a host cell.

Release of viral genes and possibly enzymes into the host cell.

Replication of viral components using host-cell machinery.

Assembly of viral components into complete viral particles.

Release of viral particles to infect new host cells.

One of the major antivirals development approach is to interfere with the ability of a virus to get into a target cell. The virus has to take a sequence of actions to do this, beginning with binding to a specific receptor molecule on the surface of the host cell and ending with the virus "un-coating" inside the cell and releasing its payload. Viruses that have a lipid envelope must also fuse their envelope with the target cell, or with a vesicle that transports them into the cell, before they can uncoat. All these steps involve the binding of viral proteins with one or more binding partners. Indeed, a number of "entry-inhibiting" or "entry-blocking" drugs are being developed to fight HIV. "Amantadine" and "rimantidine" are two entry-blockers that have been developed to combat influenza virus. Amantine and rimantadine are thought to interfere with influenza A virus M2 protein, a ion channel protein, and to inhibit virus uncoating. However, amantine and rimantadine does not work on influenza B viruses and the two drugs has been associated with gastrointestinal and central nervous system adverse effects. Pleconaril, another entry-blocker, works against rhinoviruses, which cause most colds, by blocking a pocket on the surface of the virus that controls the un-coating process. This pocket is similar in most strains of rhinoviruses, and the drug also seems to work against "entero-virus", which can cause diarrhea, meningitis, conjunctivitis, and encephalitis.

A second approach is to target the processes that synthesize virus components after a virus invades a cell. "nucleotide or nucleoside analogues" are antivirals that will interfere and block the enzymes that synthesize the RNA or DNA once the analogue is incorporated. The first successful antiviral, "acyclovir", is a nucleoside analogue, and is effective against herpes virus infections. Another nucleoside analogue named "zidovudiine" or "AZT" has been approved for treating HIV. Another class of antivirals that have been proven effective are the viral proteases inhibitors. Viral proteases act through binding to a target protein. However, protease inhibitors may have odd side-effects, for example causing fat to build up in unusual places. Then there is a need for improved protease inhibitors.

The final stage in the life cycle of a virus is the release of completed viruses from the host cell, and of course this step has also been targeted by antiviral drug developers. Two drugs named "zanamivir" and "oseltamivir" that have been recently introduced to treat influenza prevent the release of viral particles by blocking a molecule named "neuraminidase" that is found on the surface of flu viruses, and also seems to be constant across a wide range of flu strains. Those two drugs block the active site of the influenza viral enzyme neuramimidase. However Oseltamivir has been associated with adverse effects such as nausea and vomiting. Zanamivir showed adverse respiratory events in persons with chronic pulmonary disease.

Therefore there is a great need to extend the activity, the specificity and the efficacy of current antivirals, but also to extend the range of antivirals to other families of pathogens.

So far, most traditional protein-directed drug screening technologies have relied upon two assays: the radio-ligand competition assay and the cell-based reporter assay. The radio-ligand assay is based on the determination of displacement of a labelled ligand by the test compounds. The cell-based reporter assay consists in the co-transfection of the target protein gene together with a reporter gene, usually the firefly luciferase, whose expression is under the control of the protein. Such cells are then used to screen for compounds that change the reporter gene activity, indicating a specific effect of this compound on the target protein. Although already used successfully in several cases, these assays are complex (cell-based assay), time consuming (cell-based assay) and not appropriate for proteins with no known-natural ligand (ligand competition assay). Alternative simpler assays were more recently developed to overcome these limitations. These assays rely on the discovery that ligand-activated proteins specifically interact with co-activators. This discovery led to the development of the FRET-based (fluorescence resonance energy transfer) and FP-based (fluorescence polarization) assays in which the molecular interactions between the co-activator (or a fragment of it) and the target protein are measured in solutions. Although simple and amenable to high-throughput screening formats, these assays require the availability of purified and labelled proteins and co-activators. In addition, such screenings lead to the identification of ligands that directly bind to the same site as the natural protein (the ligand binding pocket). Although sometimes successful, this strategy only generates a subset of the potentially interesting ligands. Furthermore, such screening procedures usually do not allow the identification of small molecules that can discriminate between the specific isotypes of a given nuclear protein (eg. RXRα versus RXRγ nuclear receptors). Instead, selected ligands simultaneously activate or repress all protein isotypes, leading to potential side effects as already observed with some of the currently available drugs (eg. drugs targeting the retinoic acid receptor or the estrogen receptor).

It is established that ligand-binding induces a conformational change in proteins. The resolution of the crystal structures of several ligand/proteins, such as ligand/nuclear receptors, has revealed clear but distinct structural changes induced by agonists and antagonists. Such studies have also shown that these changes do dramatically influence the interaction of the protein with specific cofactors, resulting in the different biological responses observed upon treatment with agonists and antagonists. For example, it is well established that several nuclear receptor ligands may act either as agonist or as antagonists depending of the tissue. For example, Tamoxifen® acts as an antagonist of estrogen receptor alpha (ERα) in breast and is thus a potent anti-breast tumor agent, but Tamoxifen® acts also as an agonist in bones, cardiovascular organs and uterus, leading to increased risks of uterine cancer and blood clots. These tissue-specific activities of the drug are the consequences of the induction of subtle conformational changes in the target nuclear receptor, leading to specific interactions of the nuclear receptor with cofactors (co-activators or co-repressors) expressed in a tissue-specific manner.

The conformational change induced by the binding of a given ligand on a target protein has been exploited in WO 02/004956 patent application in order to predict the receptor-modulating activity of a test compound. The first step of the method is a screening of a combinatorial peptides library using the yeast two-hybrid assay in order to select a panel of conformation sensitive peptides able to bind to a target protein in the presence of several different known ligands (i.e. natural ligand, agonists, antagonists, . . . ). The binding of those peptides to the receptor is sensitive to the receptor conformation. This conformation sensitive peptides panel is then challenged for its ability to bind the target protein in the presence of an unknown test substance. The biological activity of this test substance may be predicted by the comparison of the peptides binding profile to the target protein in the presence of known reference substances. WO 02/004956 method suffers of several drawbacks. First, it does not allow the large screening of substances because of the cumbersomeness of the method. It is rather a method of predicting biological activity of already identified substances. Moreover, the selected conformation-sensitive protein-binding peptides only bind to "liganted" receptor conformation but not to the receptor in its "native" un-liganted conformation. This limitation introduces a bias that only permit to subsequently test for compounds having a predicting receptor-modulating activity which is close (i.e. "ligand-like") to the one of the known ligand (i.e. agonist or antagonist). Such tested compounds will most certainly be "ligand-like" compounds with a close mechanism of action, a close biological activity to the ligand, but also with close lack of specificity and tissue-selectivity, if any, that could lead to side effects.

The instant invention addresses all these limitations by allowing the identification of novel compounds that specifically and precisely alter the conformation of a target protein and subsequently that modify the biological activity of said target protein. In contrast to the traditional screening technologies that search for ligands that either activate or repress the receptor, this screening platform allows the isolation in a simple assay of all molecules (i.e. not only ligand-like molecules) that change the target protein conformation and may modulate the protein biological activity in a subtle manner. Besides its simplicity and sensitivity, this assay should open the way to the identification of original hits that cannot be isolated using alternative screening methods.

The present invention provides a method of selecting binding peptide(s) which binds a target protein in a native conformation, said method comprising the steps of:

a) providing a combinatorial library of peptides where said binding peptide is a member of said library, wherein said library is expressed in a plurality of cells and said cells collectively expressed all members of said library;

b) screening said library for the ability of its members to bind said target protein or a fragment thereof in a native conformation and selecting the peptides binding to said protein in native-conformation;

c) providing a known ligand of the target protein and screening of peptides selected in b) for the ability to bind to said protein in presence of said known ligand of the target protein; and d) selecting the peptide(s) screened in c) having a decrease ability to bind to said target protein in presence of said known ligand of the target protein compared to said target protein in native-conformation.

In a preferred embodiment of the method of selecting binding peptide(s) according to the present invention, step c) is repeated two times with two different known ligands of the target proteins; and step d) is a step of selecting the peptide(s) screened in c) having a decrease ability to bind to said target protein for said two known ligands of the target protein compared to said target protein in native-conformation.

In a preferred embodiment of the method of selecting binding peptide(s) according to the present invention, said step c) is repeated several times with different known ligands of the target protein.

In a preferred embodiment of the method of selecting binding peptide(s) according to the present invention, said step c) is repeated at least 3, 4, 5, 6, 7, 8, 9, 10 12 or 15, times with different known ligands of the target protein.

In a preferred embodiment of the method of selecting binding peptide(s) according to the present invention, when said step c) is repeated at least three times with different known ligands of the target protein, step d) is a selecting the peptide(s) screened in c) having a decrease ability to bind to said target protein for all said at least 2, 3, 4, 5, 6, 7, 8, 9, 10 12 or 15, known ligands of the target protein tested in step c) compared to said target protein in native-conformation.

In a preferred embodiment of the method of selecting binding peptide(s) according to the present invention, the peptide(s) selected at step d) are unable to bind to said target protein in presence of the known ligand(s) of the target protein tested in step c) but is able to bind to said protein in native-conformation.

According to the method of the invention, each cell is co-expressing:

said target protein or a ligand-binding protein moiety thereof, and one member of said library, and each cell further providing a signal producing system operably associated with said protein or moiety, such that a signal is produced which is indicative of whether said member binds said protein or moiety in or on said cell. The binding of said peptide to said protein in native conformation results in the constitution of a functional transactivation activator protein which activate expression of reporter gene, whereby a signal is produced which is indicative that said peptide binds said protein, or moiety, in or on said cell. Said signal is decreased or absent when said peptide is unable to bind specifically to said protein. The absence of specific binding of said peptide to said target protein does not allow the constitution of a functional transactivation activator protein, whereby no signal (or very few signal) is produced which is indicative that the peptide does not bind (or weakly bind) to the target protein.

By the terms "bind", it is meant herein that the peptide and the target protein interact, attach, join or associate to one another sufficiently that the intended assay can be conducted. By the terms "specific" or "specifically", it is meant herein that the peptide and the target protein bind selectively to each other and not generally to other components unintended for binding to the subject components. The parameters required to achieve specific interactions can be determined routinely, e.g. using conventional methods in the art.

The target protein of the invention may be a naturally occurring substance, or a subunit or domain thereof, from any natural source, including a virus, a microorganism (including bacterial, fungi, algae, and protozoa), an invertebrate (including insects and worms), the normal or pathological cells of an animal, especially a vertebrate (especially a mammal, bird or fish and, among mammals, particularly humans, apes, monkeys, cows, pigs, goats, llamas, sheep, rats, mice, rabbits, guinea pigs, cats and dogs), or the normal or pathological cells of a plant. The target proteins may be alternatively a non-naturally occurring protein that have been in vitro created or modified such as a mutated protein, a chimeric protein or a artificial protein. The target protein may be a glyco-, lipo-, phosphor or metalloprotein. It may be a nuclear, cytoplasmic, membrane, or secreted protein.

It is also an object of the present invention to be performed with a target which, instead of being a protein, may be a macromolecular nucleic acid, lipid or carbohydrate. If it is a nucleic acid, it may be a ribo-or a deoxyribonucleic acid, and it may be single or double stranded.

The target protein does not need to be a single macromolecule. The target protein may be a homo or hetero-multimer (dimer, trimer, tetramer, . . . ) of macromolecules. Additionally, the target protein may necessitate binding partners, such as proteins, oligo- or polypeptides, nucleic acids, carbohydrates, lipids, or small organic or inorganic molecules or ions. Examples include cofactors, ribosomes, polysomes, and chromatin.

The biological activity of the target protein is not limited to a specific activity such as a receptor or an enzymatic activity. Non limiting examples of target proteins include nuclear receptors, orphan nuclear receptor, tyrosine kinase receptors, G-protein coupled receptors, endothelin, erythropoietin receptor, FAS ligand receptor, protein kinases (protein kinase C, tyrosine kinase, serine kinase, threonine kinase, nucleotide kinase, polynucleotide kinase), protein phosphatases (serine/threonine phosphatase, tyrosine phosphatase, nucleotide phosphatase, acid phosphatase, alkaline phosphatase, pyrophosphatase), cell cycle regulators (cyclin cdk2, CDC2, CDC25, P53, RB), GTPases, Rac, Rho, Rab, Ras, endoprotease, exoprotease, metalloprotease, serine protease, cysteine protease, nuclease, polymerase, reverse transcriptase, integrase, ion channels, chaperonins (i.e. heat shock proteins), deaminases, nucleases (i.e. deoxyribonuclease, ribonuclease, endonuclease, exonuclease), telomerase, primase, helicase, dehydrogenase, transferases (peptidyl transferase, transaminase, glycosyltransferase, ribosyltransferase, acetyl transferase, guanylyltransferase, methyltransferase, . . . ), hydrolases, carboxylases, isomerases, glycosidases, deaminases, lipases, esterases, sulfatases, cellulases, lyases, reductases, ligases, . . . .

The target proteins of the invention may be structural and non-structural proteins selected among viral proteins, bacterial proteins, vegetal proteins, animal proteins and human proteins.

In a preferred embodiment, the target protein is a viral protein. Said viral protein is preferably an influenza virus protein selected among neuraminidase, protein M2 and haemagglutinin. Said viral protein is preferably a lentiviral protein, such as human immunodeficiency virus (HIV) protein, selected among reverse transcriptase, integrase, protease, TAT, NEF, REV, VIF, Vpu, Vpr. Said viral protein is preferably a hepatitis C virus protein selected among protease NS2/3, serine protease NS3-4A, NS3 RNA helicase, cofactor UA, cofactor UB, RNA polymerase 5B, non-structural protein 5A.

In a second preferred embodiment, said protein is a receptor. The term "receptor" includes both surface and intracellular receptors. Nuclear receptors are of particular interest, specially human nuclear receptor. Nuclear receptors (NR) have been previously described. (NR) are a family of ligand activated transcriptional activators. These receptors are organized into distinct domains for ligand binding, dimerization, transactivation, and DNA binding. The steroid receptor family is a large family composed of receptors for glucocorticoids, mineralo-corticoids, androgens, progestins, and estrogens. Receptor activation occurs upon ligand binding, which induces conformational changes allowing receptor dimerization and binding of co-activating proteins. These co-activators, in turn, facilitate the binding of the receptors to DNA and subsequent transcriptional activation of target genes. In addition to the recruitment of co-activating proteins, the binding of ligand is also believed to place the receptor in a conformation that either displaces or prevents the binding of proteins that serve as co-repressors of receptor function. If the ligand is a pharmacological agonist, the new conformation is one which interacts with other components of a biological signal transduction pathway, e.g.; transcription factors, to elicit a biological response in the target tissue. If the ligand is a pharmacological antagonist, the new conformation is one in which the receptor cannot be activated by one or more agonists which otherwise could activate that receptor.

A non exhaustive list of NR is described below (see FIG. 1). The NR are preferably selected among an estrogen receptor, an androgen receptor, a glucocorticoid receptor, a retinoic acid receptor alpha (RARα), a retinoic X receptor (RXR), a peroxisome proliferators-activated receptor (PPARs), a liver X receptor alpha (LXRα).

By native conformation, it is meant that the protein is not liganded to its natural ligand. Ligands are substances which bind to target proteins and thereby encompass both agonists and antagonists. However ligands exist which bind target proteins but which neither agonize nor antagonize the receptor. Natural ligands are those ligands, in nature, without human intervention, are responsible for agonizing or antagonizing or binding a natural target protein. The target protein in an un-liganded state has a particular conformation, i.e., a particular 3-D structure. When the protein is complexed to a ligand, the protein's conformation changes.

A known protein ligand is a substance known to be a ligand for the target protein. The known protein ligand of the invention is able to alter the conformation of the protein upon binding to said protein. Usually, said known protein ligand is a pharmacological agonist or antagonist of a target protein in one or more target tissues of the organism from which the target protein is coming from. However, a known protein ligand may be neither an agonist nor an antagonist of the target proteins. For example, it may be the substrate of the target protein if this latter is an enzyme. The known protein ligand may be, but need not be, a natural ligand of the protein. Said known-protein ligand of the invention is selected among known-target protein agonist and known-target protein antagonist.

According to a preferred embodiment, when the target protein is a nuclear receptor selected among:

a) estrogen receptor, then the known-protein ligand may be selected among: estradiol, diethylstilbestrol, genistein, tamoxifen, ICI182780 (Faslodex®), raloxifen; and
b) androgen receptor, then the known-protein ligand may be selected among: testosterone, dihydrotestostreone, progesterone, medroxyprogesterone acetate, cyproterone acetate, mifepristone, dehydroepiandrosterone, flutamide; and
c) glucocorticoid receptor, then the known-protein ligand may be selected among: dexamethasone, medroxyprogesterone acetate, cortivazol, deoxycorticosterone, mifepristone, fluticasone propionate, dexamethasone; and
d) Peroxisome proliferators-activated receptors (PPARs), then the known-protein ligand may be selected among the glitazones such as troglitazone; and
e) Liver X Receptor alpha (LXRα), then the known-protein ligand may be T1317 (Tularik®); and
f) Retinoic acid receptor (RAR), then the known-protein ligand may be selected among: all-trans retinoic acid, 9-cis-retinoic acid; and
g) Retinoid X receptor (RXR) then the known protein ligand may be selected at among: all-trans retinoic acid, 9-cis-retinoic acid.

According to another preferred embodiment, when the target protein is an influenza virus viral protein selected among:

a) neuraminidase, then the known-protein ligand is selected among zanamivir and oseltamivir, and
b) protein M2, then the known protein ligand is selected among amantadine and rimantadine.

According to another preferred embodiment, when the target protein is an HIV viral protein selected among:

a) viral protease, then the known protein ligand is selected among amprenavir, indinavir, saquinavir, lopinavir, fosamprenavir, ritonavir, atazanavir, nelfinavir; and
b) reverse transcriptase, then the known protein is selected among lamivudine, zalcitabine, delavirdine, zidovuline, efavirenz, didanosine, nevirapine, tenofovir disoproxil fumarate, abacavir, stavudine.

According to another preferred embodiment, when the target protein is an hepatitis C viral protein selected among:

a) NS3-4a serine protease, then the known protein ligand is selected among pyrrolidine-5,5-translactam, derivatives of 2,4,6-trihydroxy-3-nitro-benzamides, thiazolidines, benzanilides, BILN2061; and b) NS3 RNA helicase, then the known protein ligand is selected among 2,3,5-trisubstituted-1,2,4-thiadiazol-2-ium salts;

c) other hepatitis C viral proteins. Then, the known protein ligand is selected among ribavirin, levovirin, viramidine, merimpodib, thymosin alpha 1, amantadine.

The term "library" generally refers to a collection of chemical or biological entities which are related in origin, structure, and/or function, and which can be screened simultaneously for a property of interest. The term "combinatorial library" refers to a library in which the individual members are either systematic or random combinations of a limited set of basic elements, the properties of each member being dependent on the choice and location of the elements incorporated into it. Typically, the members of the library are at least capable of being screened simultaneously. Randomization may be complete or partial; some positions may be randomized and others predetermined, and at random positions, the choices may be limited in a predetermined manner. The members of a combinatorial library may be oligomers or polymers of some kind, in which the variation occurs through the choice of monomeric building block at one or more positions of the oligomer or polymer, and possibly in terms of the connecting linkage, or the length of the oligomer or polymer, too. Or the members may be non-oligomeric molecules with a standard core structure with the variation being introduced by the choice of substituents at particular variable sites on the core structure. Or the members may be non-oligomeric molecules assembled like a jigsaw pile, but wherein each piece has both one or more variable moieties (contributing to library diversity) and one or more constant moieties (providing the functionalities for coupling the piece in question to other pieces). In a "simple combinatorial library", all of the members belong to the same class of compounds (e.g., peptides) and can be synthesized simultaneously. A "composite combinatorial library" is a mixture of two or more simple libraries, e. g., DNAs and peptides, or chemical compound. Preferably, a combinatorial library will have a diversity of at least 100, more preferably at least 1,000, still more preferably at least 10,000, even more preferably at least 100,000, most preferably at least 1,000,000, different molecules.

The peptide library of the invention is a combinatorial library. The members of this library are peptides having at least three amino acids connected via peptide bonds. Preferably, they are at least four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, or thirty amino acids in length. Preferably, they are composed of less than 50, preferably less than 25 amino acids and more preferably less than 15. The peptides may be linear, branched, or cyclic, and may include non-peptidyl moieties. The amino acids are not limited to the naturally occurring amino acids.

The cells in which the peptides library are expressed is cells which, naturally or not, functionally express the suitable target protein. Preferably, the cells are eukaryotic cells. The cells may be from a unicellular organism, a multi-cellular organism or an intermediate form (slime mold). If from a multicellular organism, the latter may be an invertebrate, a lower vertebrate (reptile, fish, amphibian), a higher vertebrate (bird, mammal) or a plant. More preferably, the cells are non-mammalian eukaryotic cells. In a preferred embodiment the cells are yeast cells. Preferably, the yeast cells are of one of the following genera: *Saccharomyces, Schizosaccharomyces, Candida, Hansenula, Pichia, Kluyveromyces, Cryptococcus, Yarrowia* and *Zygosaccharomyces*. More preferably, they are of the species: *Saccharomyces cerevisiae*. In other embodiment, the cells are mammalian cells, more preferably human cells. Other non-mammalian cells of interest include plant cells (e.g. *arabidopsis*), arthropod cells, annelid or nematode cells (e.g., *Caenorhabditis elegans*; planaria; leeches; earthworms; polychaetus annelids), crustacexms (e.g., daphnia), protozoal cells (e.g. *Dictyostelium discoideum*), and lower vertebrate (reptiles, amphibians, fish) cells. In the method of the invention of selecting binding peptides, the preferred cells are yeast cells.

In a preferred embodiment, in the method of the present invention, said signal producing system is selected among signal producing system endogenous to the cell used in step a) and signal producing system exogenous to the cell.

In a preferred embodiment, in the method of the present invention, said signal producing system comprises a protein-bound component which is fused to said target protein or moiety so as to provide a chimeric protein and a peptide-bound component which is fused to said peptide so as to provide a chimeric peptide, whereby a signal is produced when the peptide-bound and protein-bound components are brought into physical proximity as a result of the binding of the peptide to the target protein.

In a preferred embodiment, in the method of the present invention, said components is a DNA-binding domain (DBD) and another of said components is a complementary transactivation domain (AD), and the signal producing system further comprises at least one reporter gene operably linked to an operator bound by said DNA-binding domain, the binding of the peptide to the target protein resulting in the constitution of a functional transactivation activator protein which activates expression of said reporter gene.

In a preferred embodiment, in the method of the present invention, said signal producing system comprises:

(i) a complementary transactivation domain (AD) which is fused to said peptide to provide a chimeric peptide; and (ii) a DNA-binding domain (DBD) which is fused to said target protein to provide a chimeric protein; and (iii) a signal producing system comprising at least a reporter gene operably linked to an operator bound by said DBD, whereby the binding of said peptide to said protein, results in the constitution of a functional transactivation activator protein which activate expression of said reporter gene, whereby a signal is produced which is indicative of the binding of said peptide to said target protein, or moiety, in or on said cell used in step a).

In a preferred embodiment, in the method of the present invention, DBD is selected from the group consisting of Gal4 and LexA and where the AD is selected from the group consisting of *E. coli* B42, Gal4 activation domain II, and HSV VP16.

In a preferred embodiment, in the method of the present invention, the reporter gene is a resistance selection gene selected from the group consisting of yeast genes HIS3, LEU2, TRP1, URA and antibiotic resistance genes.

The invention also provide a method of selecting test compound(s) having the ability to modulate the biological activity of a target protein by modify the conformation of said target protein, comprising the steps of:

A) selecting at least one peptide by the method of the invention, said peptide having a decrease or no ability to bind to said target protein in presence of known ligand of the target protein compared to said target protein in native-conformation;

B) screening a library of test compounds for their ability to alter the binding of the peptide(s) selected in step a) to said target protein in native conformation; According to a preferred embodiment, the test compound is exogenously added to the cell. Alternatively, the test compound is present or injected into the cells; and C) selecting test compound(s) that alter the binding of said peptide(s), wherein a decrease in the binding or an absence of binding is indicative that the test compound induces a conformational change of the target protein.

In a preferred embodiment, the present invention is directed to a method of selecting test compound(s) having the ability to modulate the biological activity of a target protein by modifying the conformation of said target protein, according to the invention, characterized in that the method comprises in addition:

a step D) wherein the test compound(s) selected in step C) is tested for its agonist or antagonist activity by a method allowed to know whether a ligand of a target protein, preferably a receptor, is an agonist or an antagonist of a the biological activity of a target protein; and a step E) wherein the test compound(s) selected in step C) is finally selected if said compound is not an agonist and an antagonist of the biological activity of said target protein.

The methods for testing if a ligand of a target protein is an agonist or an antagonist, particularly for a receptor protein, are well known for the skill person in the art.

Among the assays which can distinguish between agonists and antagonists activity, cell-based assays and reporter gene systems can be cited and are referred (McDonnell, et al., Molec. Endocrinol., 9:659 (1995)). In these systems, the receptor and a reporter gene are co-transfected into cells in culture. The reporter gene is only activated in the presence of active receptor. The ability of a compound to modulate receptor activity is determined by the relative strength of the reporter gene activity.

Methods have been developed that also take advantage of the different conformational states of receptors. Proteolytic digestion of receptor in the presence of an agonist or antagonist produces distinct banding patterns on a denaturing polyacrylamide gel. In certain conformations, the receptor is protected from digestion at a particular site, while a different conformation may expose that site. Thus the banding patterns may indicate whether the receptor was complexed with an agonist or antagonist at the time of proteolytic digestion.

The following documents disclosing cell based screening methods can be also cited:

U.S. Pat. No. 5,723,291—Methods for screening compounds for estrogenic activity;

U.S. Pat. No. 5,298,429-Bioassay for identifying ligands for steroid hormone receptors;

U.S. Pat. No. 5,445,941—Method for screening anti-osteoporosis agents;

U.S. Pat. No. 5,071,773—Hormone receptor-related bioassays;

U.S. Pat. No. 5,217,867—Receptors: their identification, characterization, preparation and use.

In the method of selecting test compound(s) having the ability to modulate the biological activity of a target protein, the screening of the library of test compounds at step B), is performed in a cell, not integrated into a whole multi-cellular organism or a tissue or organ of an organism. Said cell is co-expressing said target protein, or a ligand-moiety thereof, and said peptide. This peptide is able to bind to the target protein in its native conformation but not into a liganted conformation. The peptide is preferably selected by the method of the invention.

Said cell further comprises a signal producing system operably associated with said protein or moiety whereby:

the binding of said peptide to said protein in presence of test compound results in the constitution of a functional trans-activation activator protein which activate expression of said reporter gene, whereby a signal is produced which is indicative that said peptide binds said protein, or moiety, in or on said cell, and that said compound does not modify the conformation of target protein; or the decrease or the absence of binding of said peptide to said protein in presence of the test compound does not allow the constitution of a functional transactivation activator protein, whereby no signal or very few signal is produced which is indicative that said test compound modify the conformation of target protein.

A signal is "produced" when said signal is detectable by the means adapted and normally used by the man skilled in the art to perform the detection (i.e. human eye, spectrophotometer, etc.).

The indication that an absence of binding had occurred is when the signal is no longer detectable by the means routinely used to detect the reporter gene expression by the man skilled in the art. The indication that a decrease in the binding had occurred is when the decrease of the signal generated by the reporter gene expression is at least 50%, preferably at least 75%, and more preferably at least 90% of the signal generated when the specific binding occurred.

The method of selecting test compound is performed in vitro in cells, which are not integrated into a whole multicellular organism or a tissue or organ of an organism. Said cells are preferably cells where the target protein is naturally or not expressed in and/or biologically functional in. The cells may be the same cells as used to perform the screening of the peptides library to isolate binding peptides. However, in a first preferred embodiment, said cells are selected among human primary cells, human embryonic cells and human cell lines. In a preferred embodiment, human cells are continuous human cell lines; non-limiting examples of human cell lines includes Hela, T47D, A549, HEK-293, MCF7. Alternatively, said human cells are embryonic cells, preferably embryonic cells selected among totipotent cells (i.e. Embryonic Stem cells, ES cells), pluripotent, multipotent and unipotent cells. In a specific embodiment, the cell is a human ES cells and the target protein is a key protein involve in the control of a differentiation pathway of ES cells to human differentiated cells. In a second embodiment, said cells are selected among animal cells such as animal primary cells, animal embryonic cells and animal cell lines. Non limiting examples of animal cell lines includes VERO, CHO, NSO, COS and 3T3.

The signal producing system of the methods of the invention is selected among signal producing system endogenous to the cell and signal producing system exogenous to the cell. Preferably, said signal producing system is endogenous to the cell. The signal producing system comprises a protein-bound component which is fused to said target protein or moiety so as to provide a chimeric protein and a peptide-bound component which is fused to said peptide so as to provide a chimeric peptide, whereby a signal is produced when the peptide-bound and protein-bound components are brought into physical proximity as a result of the binding of the peptide to the target protein. Said components is a DNA-binding domain (DBD) and another of said components is a complementary transactivation domain (AD), and the signal producing system further comprises at least one reporter gene operably linked to an operator bound by said DNA-binding domain, the binding of the peptide to the target protein resulting in the constitution of a functional transactivation activator protein which activates expression of said reporter gene. Said signal producing system of the invention comprises:

(i) a complementary transactivation domain (AD) which is fused to said peptide to provide a chimeric peptide. The AD is preferably selected from the group consisting of *E. coli* B42, Gal4 activation domain II, and HSV VP16; and (ii) a DNA-binding domain (DBD) which is fused to said target protein to provide a chimeric protein; the DBD is preferably selected from the group consisting of Gal4 and LexA; and (iii) a signal producing system comprising at least one reporter gene operably linked to an operator bound by said DBD, whereby the binding of said peptide to said protein, results in the constitution of a functional transactivation activator protein which activate expression of said reporter gene(s), whereby a signal is produced which is indicative of the binding of said peptide to said target protein, or moiety, in or on said cell.

When the signal is the death or survival of the cell in question, the assay is said to be a selection. When the signal merely results in detectable phenotype by which the signalling cell may be differentiated from the same cell in a non-signalling state, the assay is a screen. However the term "screening" in the present invention may be used in a broader sense to include a selection. According to the present invention, "reporter gene" means a gene, the expression of which in one cell, allows to detect said cell in a large population of cells; that is to say, that it allows to distinguish between the cells that are expressing or not said reporter gene. The reporter gene of the invention includes detectable phenotype reporter genes and resistance selection genes. Non-limiting examples of resistance selection genes include yeast genes: 3-isopropylmalate dehydrogenase (LEU2), phosphoribosylanthranilate isomerase (TRP1) and imidazole-glycerol-phosphate dehydratase (HIS3) and antibiotic resistance genes. Among the antibiotics, one can recite, neomycin, tetracycline, ampicilline, kanamycine, phleomycine, bleomycine, hygromycine, chloramphenicol, carbenicilline, geneticine, puromycine, blasticidine. The antibiotics resistance gene are well known to the man skilled in the art. For example, neomycine gene provides the cells with a resistance to G418 antibiotic added to the cell culture medium. Alternatively, non-limiting examples of detectable phenotype reporter genes include the following genes: DHFR, luciferase, chloramphenicol acetyltransferase, beta-lactamase, adenylate cyclase, alkaline phosphatase, and beta-galactosidase, and auto-fluorescent proteins (such as green fluorescent protein, red fluorescent protein, blue fluorescent protein, yellow fluorescent protein, and all the variants and derived fluorescent proteins). The signal producing system may include, besides reporter gene(s), additional genetic or biochemical elements which cooperate in the production of the signal. Such an element could be, for example, the substrate of a reporter gene which an enzyme.

There may be more than one signal producing system, and the system may include more than one reporter gene.

According to a preferred embodiment, the method of selecting binding peptides of the invention is performed in yeast cells, and the signal producing system is comprising at least two reporter genes in tandem, one resistance selection gene selected among HIS3, LEU2, TRP1, and one reporter gene selected among luciferase, auto-fluorescent proteins and beta-galactosidase.

In another preferred embodiment, the method of selecting test compounds of the invention is performed in human cells and the signal producing system is comprising at least one reporter gene selected among luciferase, auto-fluorescent proteins and beta-galactosidase.

The present invention also relates to the test compounds selected by the method of the invention. Preferably the test compounds are small organic molecules, e.g., molecules with a molecular weight of less than 2000 daltons, preferably less than 1000 daltons, more preferably less than 500 daltons, which are pharmaceutically acceptable. The library of test compounds comprises at least 10,000 compounds, at least 100,000 compounds, at least 1 million compounds, at least 10 millions compounds. Test compounds are preferably of chemical classes amenable to synthesis as a combinatorial library. This facilitates identification of test compounds which bind the protein in vitro and it allows to make related compounds (derivatives, variants, . . . ) for testing if a test compound proves of interest.

The test compounds that are selected by the method of the invention includes substances which are similar or "ligand-like" to the substances already identified as having the ability to specifically bind the target protein such as potential pharmacological agonists, antagonists, co-activators and co-inhibitors for the protein in question. Such "ligand-like" test compounds may have a close mechanism of action and a close biological activity to the known-protein ligand, with the potential side effects of the known-protein ligands (agonist or antagonist). More importantly, the test compounds that are selected by the method of the invention includes substances which are not similar to the substances already identified as having the ability to specifically bind the target protein, because the method of the invention identified binding peptides in their native conformation in opposition to the methods of the prior art. Said latter compounds, which are not ligand-like molecule, are expected to have different biological and pharmacological properties compared to the known protein ligand. Alternatively the test compounds may be the binding peptides or a variant thereof, or chemical molecules that mimic said binding peptides, identified by the method of the invention.

The present invention also relates to the use of the selected test compounds of the invention as an assay hit for the identification of hits which constitute new candidate molecule(s) for drug development. The invention also relates to the use of selected test compounds of the invention as a drug, especially for the prophylactic and therapeutic treatment of diseases, such as, without limitation and as examples, human and animal viral diseases and human and animal cancers.

In another aspect, the present invention is directed to an isolated selected binding peptide which binds a target protein in a native conformation and which has a decrease ability to bind to said protein in presence of known ligand(s) of the target protein compared to said protein in native-conformation selected by the corresponding method of the present invention, characterized in that it is selected from the group consisting of the peptides having the sequence SEQ ID NO 17, SEQ ID NO 18, SEQ ID NO 19, SEQ ID NO 20, SEQ ID NO 21, SEQ ID NO 22 and SEQ ID NO 23, or a variant thereof.

By variant of the peptides of the present invention, it is intended to include peptides whose sequences differing from the above sequences are only by no more than one nonconservative substitution and/or one or more conservative substitutions, preferably no more than a single conservative substitution. The substitutions may be of non-genetically encoded (exotic) amino acids, in which case the resulting peptide is nonbiogenic. Preferably, the variants are biogenic.

By variant it is also intended to designate peptides whose sequences of the peptides may be obtained by systematic truncation of the peptides of the present invention, starting at the N-terminal, the C-terminal, or both simultaneously or sequentially. The truncation may be one amino acid at a time, but preferably, to speed up the process, is of 10 of the peptide at one time. If a given truncation is unsuccessful, one retreats to a less dramatic truncation intermediate between the last successful truncation and the last unsuccessful truncation.

Preferably, the variants as defined above are peptides having the ability to bind the target protein of its parent peptide of the invention and to have its binding decreased in presence of the known ligand(s) of the target protein, as for its parent peptide of the invention.

In another aspect, the present invention is also directed to an isolated peptide selected from the group consisting of the peptides having the sequence SEQ ID NO 17, SEQ ID NO 18, SEQ ID NO 19, SEQ ID NO 20, SEQ ID NO 21, SEQ ID NO 22 and SEQ ID NO 23, or a variant thereof, as a medicament.

In another aspect, the present invention is also directed to the use of a peptide selected from the group consisting of the peptides having the sequence SEQ ID NO 17, SEQ ID NO 18 and SEQ ID NO 19, or a variant thereof, for the preparation of a composition for the prevention or the treatment of hypofertility, breast cancer, cardiovascular diseases or osteoporosis.

In another aspect, the present invention is also directed to the se of a peptide selected from the group consisting of the peptides having the sequence SEQ ID NO 20, SEQ ID NO 21, SEQ ID NO 22 and SEQ ID NO 23, or a variant thereof, for the preparation of a composition for the prevention or the treatment of human cancers, preferably the promyelocytic leukaemia.

The main limitation in the method of selecting binding peptides of the invention is the availability of known ligands (i.e drugs) to identify conformation sensitive peptides. In the virus field for example, it is often the case that no antiviral drug is known to bind to a viral target protein. However, since viruses are intracellular parasites which are using the cellular machinery for their replication, viral proteins are interacting with host cell proteins or molecules (ATP, tRNA, ribosomes, cell enzymes . . . ). Interactions of numerous virus proteins with those of the host cells have been reported in the scientific literature (Tellinghuisen & Rice Curr Opin Microbiol. 2002, 5: 419-427; HIV-1, Human proteins interaction database, National Institute of Allergy & Infectious Diseases; Lo et al. J. Virol. 1996 Aug. 70(8):5177-82). According to another embodiment of the invention, when no ligand (i.e. pharmacological agonists or antagonists) is known to bind to the target proteins, either cellular or viral proteins interacting with the target protein might be used instead to identify conformation sensitive peptides. Once peptides interacting with the target protein are identified, an expression vector encoding the protein interacting with the target protein is introduced in the yeast already modified with an expression vector encoding the target protein and an expression vector encoding the peptide library. Peptides that will be blocked by the protein/protein interaction, either due to the conformation modification of the target or due to the inaccessibility of their recognition site on the target protein due to a steric hindrance, will be identified. The invention also relates to a method of selecting binding peptide(s) which binds a target protein in a native conformation, said method comprising the steps of:

a) providing a combinatorial library of peptides where said binding peptide is a member of said library, wherein said library is expressed in a plurality of cells and said cells collectively expressed all members of said library;
b) screening said library for the ability of its members to bind said target protein in a native conformation and selecting the peptides binding to said protein in native-conformation;
c) screening of peptides selected in b) for the ability to bind to said protein in presence of one protein known to interact with the target protein; and,
d) selecting the peptides screened in c) having a decrease ability or no ability to bind to said target protein in presence of said protein known to interact with the target protein, compared to said protein in native-conformation.

If proteins interacting with the target protein are not known, the man of the art knows how to identify proteins that are able to interact with a target protein. The yeast two-hybrid is a validated technology to identify protein-protein interactions. For example, cDNA clones encoding proteins interacting with the target protein can be isolated with a yeast two-hybrid screen of a cDNA library from human cells of interest. Human cDNA library could be commercially available or will have to be constructed.

Alternatively, the selection of the binding peptide of the invention may be performed by using mutated target proteins (i.e deletion, mutation, point mutation, etc. . . . ). Indeed mutations of viral proteins have been described that modify the conformation of the protein (Labonté et al. J Biol. Chem. 2002 Oct. 11; 277(41):38838-46; Zhu et al, Proc Natl Acad Sci USA. 2001 Dec. 18; 98(26):15227-32; Gruenke et al, J. Virol. 2002 May; 76(9):4456-66). Those mutants would be useful to validate that peptides are conformation sensitive peptides. In the absence of ligands (i.e. agonist, antagonists) known to interact with the target protein, mutated target proteins may also could be used to identify conformation sensitive peptides. According to another embodiment, the invention also relates to a method of selecting binding peptide(s) which binds a target protein in a native conformation, said method comprising the steps of:

a) providing a combinatorial library of peptides where said binding peptide is a member of said library, wherein said library is expressed in a plurality of cells and said cells collectively expressed all members of said library;
b) screening said library for the ability of its members to bind said target protein in a native conformation and selecting the peptides binding to said protein in native-conformation;
c) screening of peptides selected in b) for the ability to bind to a mutated form of the target protein; and,
d) selecting the peptides screened in c) having a decrease ability or no ability to bind to said mutated target protein compared to the target protein in native-conformation.

The techniques of introducing mutations in proteins are well known to the man skilled in the art and can be done either by biological, physical or chemical means. Alternatively, such mutated proteins may be natural variants of the wild type proteins.

For the remainder of the description, reference will be made to the legend to the figures below.

BRIEF DESCRIPTION OF THE DRAWINGS

FIG. 1: Unified nomenclature system for human nuclear receptors (Shiau et al., 2002, Curr. Opin. Drug Disc. Dev., 4, 575-590)

FIG. 5: Amino acid sequences of ERα conformation sensitive peptides selected Amino-Acid sequence of three selected ERα 3D-screen peptides: 30-2; 5-21; 9-23. Interestingly, two independently selected ERα conformation sensitive peptides displayed the same sequence.

FIG. 7: Amino acids sequences of RARα conformation sensitive peptides selected Amino-Acid sequence of four selected RARα 3D-screen peptides: I-B8, I-C8, III-D2 and II-F8.

FIG. 9B. Dissociation of the conformation sensitive peptide from the target protein in the liganded state: High-Through-put-Screening (HTS) of small molecule libraries on this human cell platform will allow the identification of chemical compounds (hits) that are able to bind to the target protein, change its conformation and exclude the conformation sensitive peptide/VP16-AD protein from the complex. As a result, expression of the reporter gene will be prevented. Isolated hits will then be reconfirmed, further characterized and optimized into therapeutically relevant chemical leads.

Figure 2:
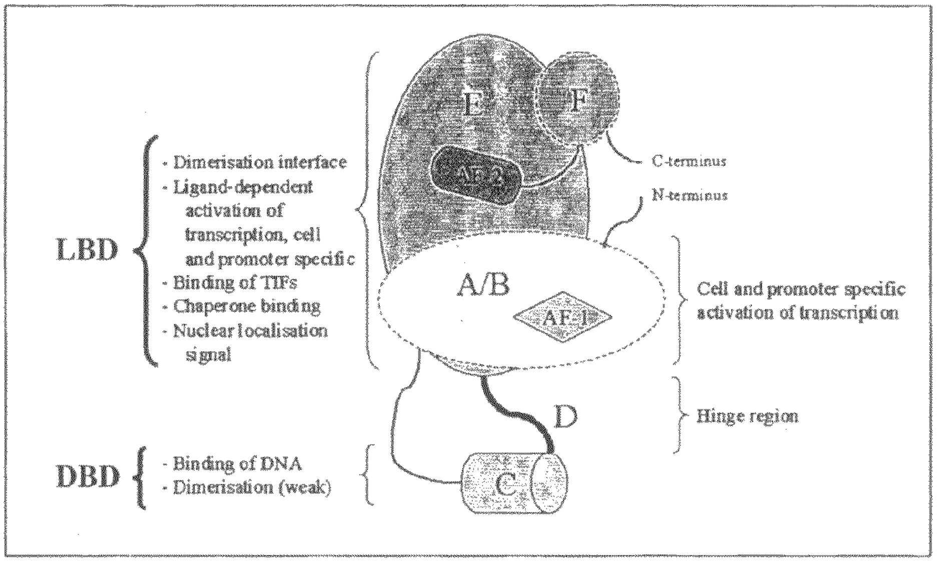
FIG. 2: Schematic representation of the modular structure of nuclear receptors This scheme presents the different domains of the receptor, and their respective functions. Not all nuclear receptors contain all regions. AF-1 and AF-2 are the two major activation functions found in many nuclear receptors. (Steinmetz et al. 2001, Ann. Rev. Biophys. Biomol. Struct., 30, 329).

Hela cells are transiently transfected with three expression plasmids encoding the reporter gene luciferase (eg. UAS-Luc), the ERα fused to a DNA Binding Domain (DBD) and the conformation sensitive peptide previously screened in yeast and fused to the VP16-AD, respectively, with the jetPEI reagent. Cells are grown in the absence of any ligand (DMSO, lane 1; ethanol, lane 2), or in the presence of ER ligands (agonists E2, DES or antagonists 4OHT, lane 3-5) or non-ER ligands (Dex and 9C-RA; lanes 8 & 9), or in the presence of Estren (lane 6) at 100 nM (right panel) and 10 μM (left panel). Luciferase expression is measured after 24 H. Luciferase expression is strong in absence of ligands and in presence of non-ER ligands. In constrast, addition of ER ligands, either agonists or antagonists, as well as addition of Estren, induce ERα conformational changes that dissociate the 3D-sensor/VP16AD protein from the receptor, preventing the expression of luciferase.

Figure 12:
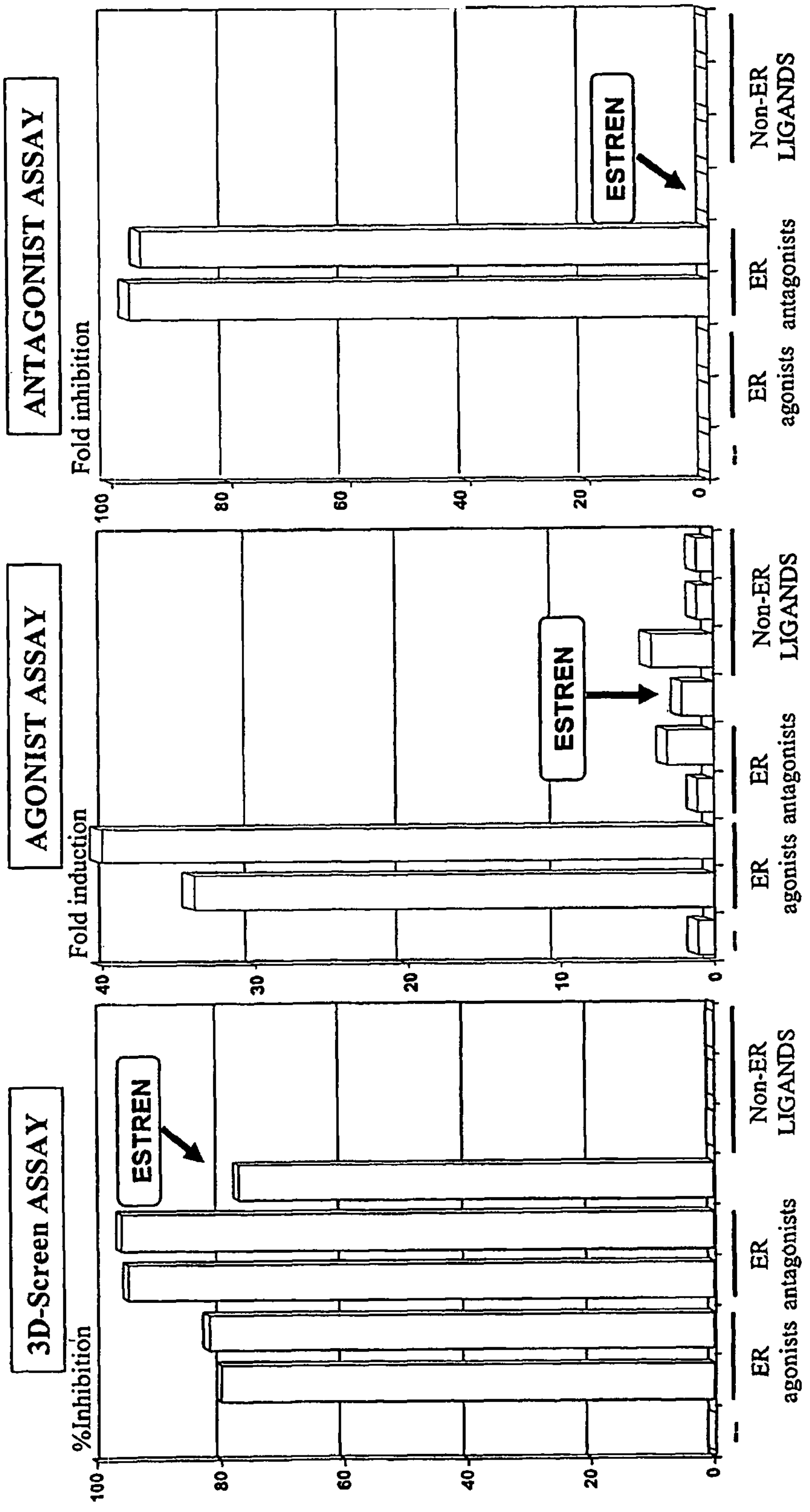

FIG. 12: Comparison of ESTREN detection with 3D-screen platform, standard agonist assay and standard antagonist assay Estren molecule has been identified as an allosteric modulator of ERα by using 3D-screen platform of the present invention. Standard agonist and antagonist assay performed in the pharmaceutical industry do not allow the identification of Estren.

Figure 13:
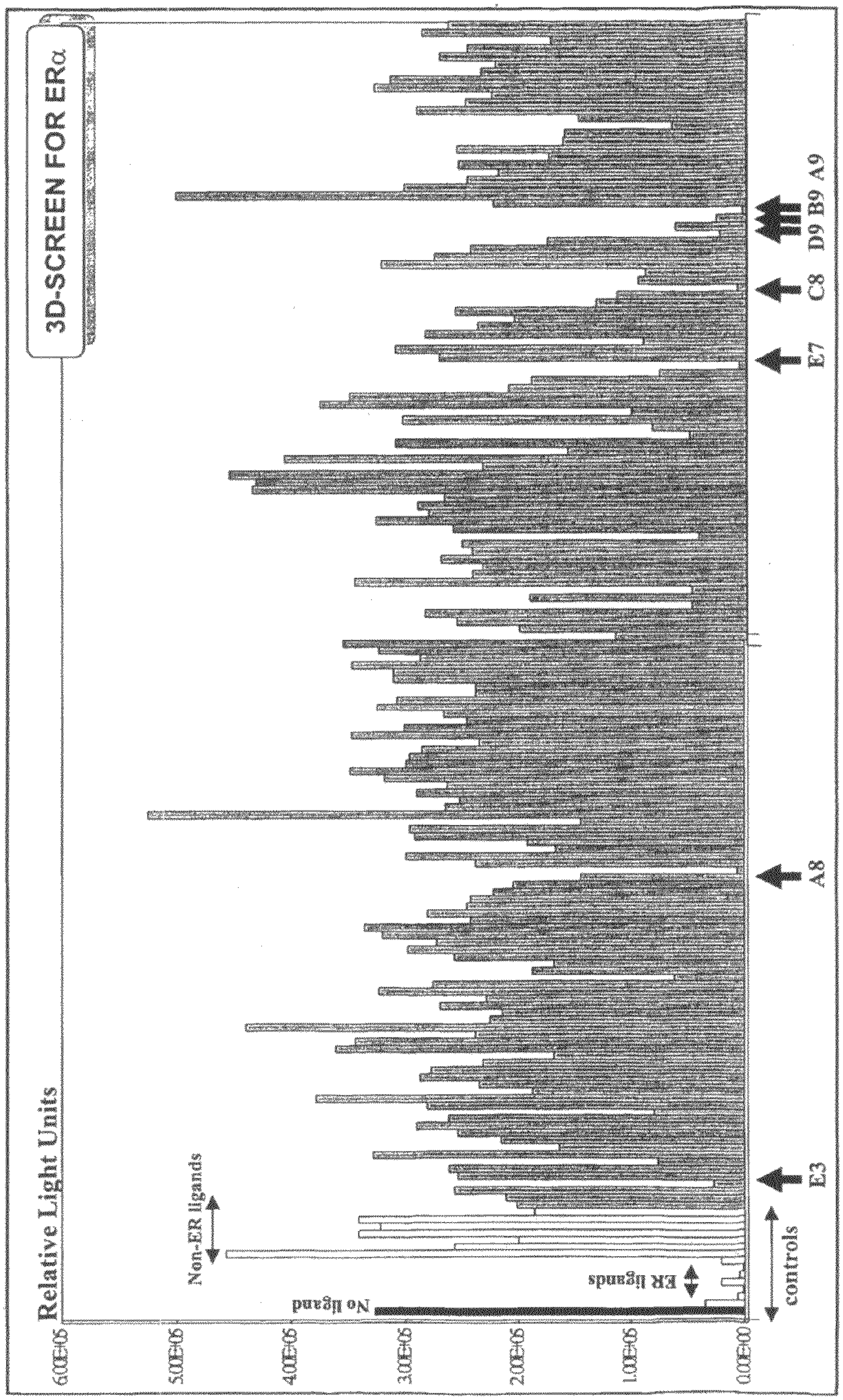

FIG. 13: Generation of a 3D-sensor human cell screening platform for ERα

Hela cells are transiently transfected with three expression plasmids encoding the reporter gene luciferase (eg. UAS-Luc), the ERα fused to a DNA Binding Domain (DBD) and the conformation sensitive peptide previously screened in yeast and fused to the VP16-AD, respectively, with the jetPEI reagent. Cells are grown in the absence of any ligand (DMSO, lane 1), or in the presence of ER ligands (agonists E2, DES, GEN or antagonists 4OHT, ICI182780, Raloxifen; lanes 2-7), or non-ER ligands (9C-RA and AT-RA; lanes 8 & 9; dexamethasone, lane 10; PPARγ ligands, lanes 11-14) at 10 μM. Luciferase expression is measured after 24 H. Luciferase expression is strong in absence of ligands and in presence of non-ER ligands. In constrast, addition of ER ligands, either agonists or antagonists or allosteric modulator, induces ERα conformational changes that dissociate the 3D-sensor/VP16AD protein from the receptor, preventing the expression of luciferase.

Figure 14:
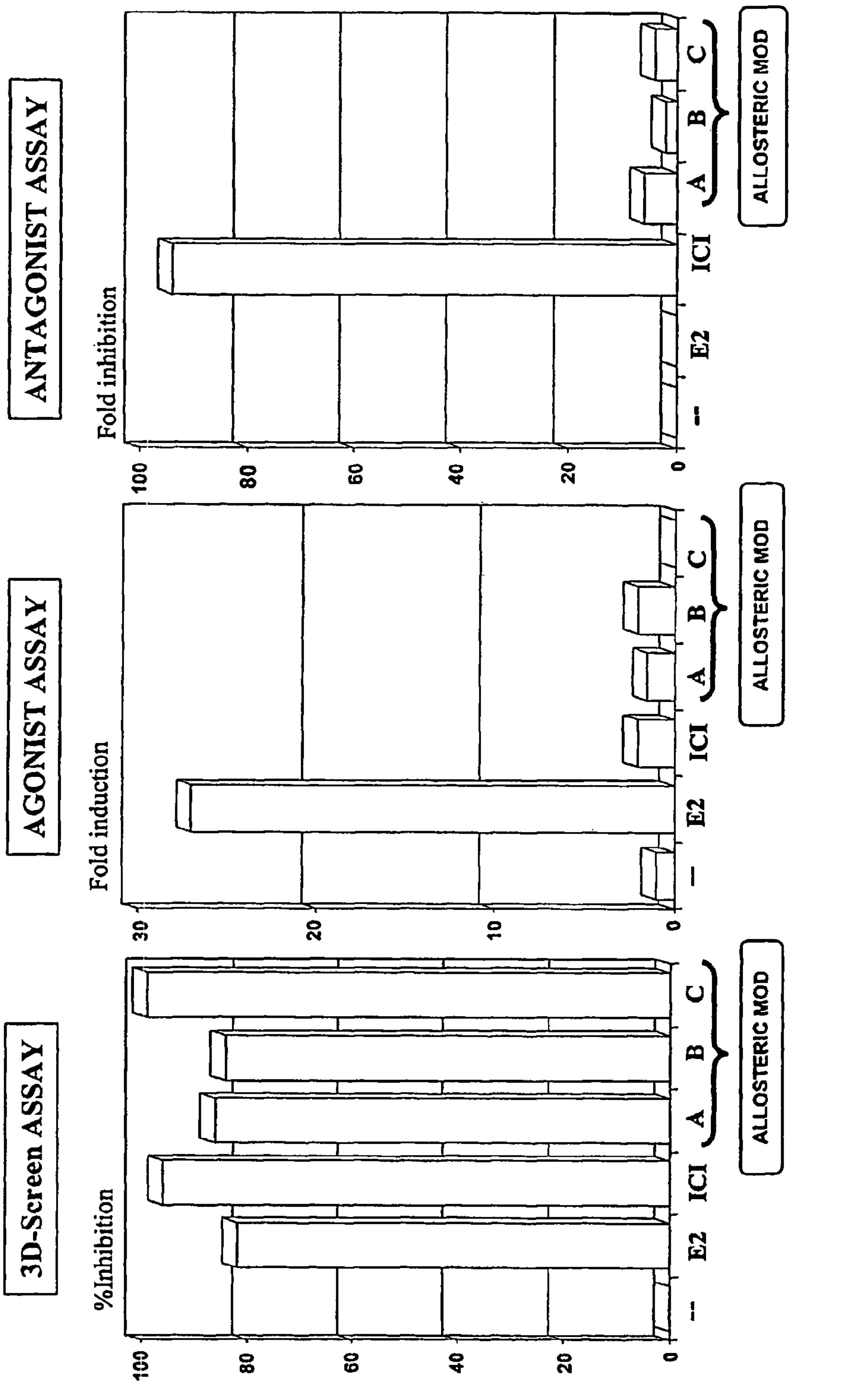

FIG. 14: Comparison of detection of 3 different hits identified with 3D-screen platform with standard agonist and antagonist assays Molecule A, B and C has been previously identified (see FIG. 13) as an allosteric modulator of ERα by using 3D-screen platform of the present invention. Standard agonist and antagonist assay performed in the pharmaceutical industry do not allow the identification of such hits.

EXAMPLES

Example 1

Generation of Random Peptides Libraries

The peptide libraries are generated in *E. coli* by inserting randomly synthesized oligonucleotides in fusion with the carrier protein such as VP16-AD. Oligonucleotides oVV1261 (or oVV1262), oVV1259 and oVV1260 (Table I) are mixed at a molar ratio of 1:50:510 (0.8 μl:40 μl:40 μl from oligonucleotide stocks at 100 μM) and annealed in 20 mM Tris-HCl pH7.5; 2 mM $MgCl_2$; 20 mM NaCl in a final reaction volume of 110 μl by using a PCR cycler (1 cycle at 94° C. for 5 minutes/70° C. for 5 minutes/65° C. for 5 minutes/60° C. for 5 minutes/55° C. for 5 minutes/50° C. for 5 minutes/45° C. for 5 minutes/40° C. for 5 minutes/35° C. for 5 minutes/30° C. for 5 minutes/25° C. for 5 minutes/20° C. for 5 minutes/150° C. for 5 minutes/10° C. for 5 minutes/4° C. for ever).

TABLE I

| sequence of oligonucleotides used to generate the peptide libraries | | |
|---|---|---|
| oVV1259 | 5'-CGGCCACGCTGGA-3' | SEQ ID No 1 |
| oVV1260 | 5'-TGAATAAATAGGCCATAA-3' | SEQ ID No 2 |
| oVV1261 | 5'-TGGCCTATTTATTCA $(VNN)_{15}$ TCCAGCGTGGCCGCCT-3' | SEQ ID No 3 |
| oVV1262 | 5'-TGGCCTATTTATTCA $(VNN)_5$ TCCAGCGTGGCCGCCT-3' | SEQ ID No 4 |

The random oligonucleotide mix encoding the peptides is then fused to the carboxy-terminus of the VP16-AD carrier protein, in a yeast expression vector containing a yeast promoter (eg. constitutive promoter of ADH1 or PGK1 genes, or galactose-inducible promoter Gal1) and a yeast terminator (eg. terminator sequences of ADH1 or PGK1 genes). The vector backbone composed of the ADH1 promoter, the VP16 trans-activation domain and the ADH1 terminator was preferentially used in these experiments but any other promoter, trans-activation domain, carrier protein and terminator sequences can similarly be used to develop peptide libraries. Ligation between the vector and the annealed oligonucleotides is done by unidirectional SfiI cloning at a vector/insert ratio of 10:1 and the ligation product is then transformed into *E. coli* by electroporation. The diversity of the peptide library is analyzed by plating serial dilutions of the *E. coli* transformation mix. The diversity of the library is about $6.10^7$.

To improve the library diversity, the random amino-acid codon VNN as in oVV1261 and oVV1262 can be replaced by $VNN_n$, where n is any number of random codons. This not only reduces the termination signal from 3 to 1, but also decreases disproportionate representation of certain amino-acids from 1:6 to 1:3.

Example 2

Construction of "Bait" Encoding Vectors for Yeast Two-Hybrids Experiments

For yeast two-hybrids experiments, the cDNAs encoding either the full-length target protein [i.e a nuclear receptor, a viral protein] or a fragment thereof, [for example a nuclear receptor fragment such as the LBD] fused in frame to a beterologous DNA Binding Domain (eg. the DBD of the bacterial LexA protein) were inserted in a yeast expression vector under the control of yeast promoter and terminator regulatory signals (eg. control signals from the ADH1 gene).

2.1—Bait ERα Expression Vector

The cDNAs, encoding either the full-length, (fl) estrogen receptor alpha (ERα) or a fragment thereof (eg. DEF region of ERα that includes LBD) fused in frame to a heterologous DBD of the bacterial LexA protein, were inserted in a yeast expression vector under the control of yeast ADH1 gene promoter and yeast ADH1 gene terminator regulatory signal. The bait plasmids constructed for the ERα target protein were expressed either as a fusion protein between the LexA-DBD and the full-length receptor (fl) or as fusion protein between the LexA-DBD and the receptor DEF regions (including the LBD). The resulting plasmids are hereafter called bait-ER(fl) and bait-ER(DEF).

2.2—Bait RARα Expression Vector

The cDNAs, encoding either the full-length (fl) Retinoic Acid Receptor alpha (RARα) or a fragment thereof (eg. DEF region of RARα that includes LBD) fused in frame to a heterologous DBD of the bacterial LexA protein, were inserted in a yeast expression vector under the control of yeast ADH1 gene promoter and yeast ADH1 gene terminator regulatory signal. The bait plasmids constructed for the ERα target protein were expressed either as a fusion protein between the LexA-DBD and the full-length receptor (fl) or as fusion protein between the LexA-DBD and the receptor DEF regions (including the LBD). The resulting plasmids are hereafter called bait-RAR(fl) and bait-RAR(DEF).

2.3—Bait HCV NS5B Expression Vectors

The non-structural protein 5B (NS5B) (SEQ ID N° 5) of hepatitis C virus (HCV) (molecular weight: 65 kD) has an RNA-dependent RNA polymerase activity. NSSB is located at the C-terminal region of the HCV poly-protein. It plays an essential role for the viral replication. It is thought that RNA-dependent RNA synthesis takes place by a copy back mechanism, in which the 34 nucleotides of the template is used to prime synthesis of the complementary strand. The RNA polymerase NS5B constitutes a major target for the development of antiviral therapies. Inhibition of the enzyme would disrupt HCV RNA strand synthesis preventing viral replication.

Séquence ID N°5
Gène NS5B 1b (full length)
Origin: HCV

```
ATGTCAATGTCCTACACATGGACAGGTGCCTTGATCACGCCATGCGCTGC

GGAGGAGAGCAAGTTGCCCATCAATCCGTTGAGCAACTCTTTGCTGCGTC

ACCACAGTATGGTCTACTCCACAACATCTCGCAGCGCAAGTCTGCGGCAG

AAGAAGGTAACCTTTGACAGAATGCAAGTCCTGGACGACCACTACCGGGA

CGTGCTCAAGGAGATGAAGGCGAAGGCGTCCACAGTTAAGGCTAGGCTTC

TATCTATAGAGGAGGCCTGCAAACTGACGCCCCCACATTCGGCCAAATCC

AAATTTGGCTACGGGGCGAAGGACGTCCGGAGCCTATCCAGCAGGGCCGT

CAACCACATCCGCTCCGTGTGGGAGGACTTGCTGGAAGACACTGAAACAC

CAATTGATACCACCATCATGGCAAAAAATGAGGTTTTCTGCGTCCAACCA

GAGAAAGGAGGCCGCAAGCCAGCTCGCCTTATCGTATTCCCAGACCTGGG

GGTACGTGTATGCGAGAAGATGGCCCTTTACGACGTGGTCTCCACCCTTC

CTCAGGCCGTGATGGGCCCCTCATACGGATTCCAGTACTCTCCTGGGCAG

CGGGTCGAGTTCCTGGTGAATACCTGGAAATCAAAGAAATGCCCTATGGG

CTTCTCATATGACACCCGCTGCTTTGACTCAACGGTCACTGAGAATGACA

TCCGTACTGAGGAGTCAATCTACCAATGTTGTGACTTGGCCCCCGAAGCC

AGACAGGCCATAAAGTCGCTCACAGAGCGGCTCTACATCGGGGGTCCCCT

GACTAATTCAAAAGGGCAGAACTGCGGTTATCGCCGGTGCCGCGCGAGCG

GTGTGCTGACGACTAGCTGCGGCAATACCCTCACATGCTACTTGAAAGCC
```

-continued

```
ACTGCGGCCTGTCGAGCTGCAAAGCTCCAGGACTGCACGATGCTCGTGAA

CGGAGACGACCTTGTCGTTATCTGCGAAAGCGCGGGAACCCAGGAGGATG

CGGCGAGCCTACGAGTCTTCACGGAGGCTATGACTAGGTACTCTGCCCCC

CCCGGGGACCCGCCCCAACCAGAATACGACTTGGAGGTGATAACGTCATG

CTCCTCCAATGTGTCGGTCGCGCACGATGCATCGGGCAAAAGGGTGTACT

ACCTCACCCGTGACCCCACCACCCCCCTCGCACGGGCTGCGTGGGAGACA

GTTAGACACACTCCAGTCAACTCCTGGCTAGGCAATATCATCATGTATGC

GCCCACCCTATGGGCGAGGATGATTCTGATGACTCATTTCTTCTCTATCC

TTCTAGCTCAGGAGCAACTTGAAAAAGCCCTGGATTGTCAGATCTACGGG

GCCTGCTACTCCATTGAGCCACTTGACCTACCTCAGATCATCGAACGACT

CCATGGTCTTAGCGCATTTTCACTCGATAGTTACTCTCCAGGTGAGATCA

ATAGGGTGGCTTCATGGCTCAGGAAACTTGGGGTACCGCCCTTGCGAGTC

TGGAGACATCGGGCCAGAAGTGTCCGCGCTAAGCTGCTGTCCCAGGGGGG

GAGGGCCGCCACATGCGGCAAATACCTCTTCAACTGGGCAGTAAGGACCA

AGCTTAAACTCACTCCAATCCCGGCTGCGTCCCAGCTAGACTTGTCCGGC

TGGTTCGTTGCTGGTTACAACGGGGGAGACATATATCACAGCCTGTCTCG

TGCCCGACCCCGTTGGTTCATGTTGTGCCTACTCCTACTTTCTGTAGGGG

TAGGCATCTACCTGCTCCCCAACCGGTAA
```

2.3.1—A plasmid containing HCV NS5B full-length genotype 1b (Séquence ID N° 5) and a plasmid containing HCV NS5B Δ 21 were used as templates to produce HCV NS5B full length and HCV NS5B Δ 21 by PCR with oligonucleotides primers containing appropriate restriction sites (BamHI and XhoI for NS5B full length and PstI and XhoI for NS5B Δ 21). A truncated HCV NS5B protein is used in the present study because it has been shown that the deletion Δ 21 in C-terminal region of HCV NS5B enhances protein solubility and protein expression (Yamashita et al., 1998 JBC Vol. 273 N° 25, pp 15479-15486).

The oligonucleotides primers used are the following:

```
Forward primer:
                                        (SEQ ID No 6)
5' TATCTCGAGTCAATGTCCTACACATGGACAGGTG 3'.

NS5B Δ 21 Reverse primer:
                                        (SEQ ID No 7)
5'AGATCTGCAGTTAACGGGGTCGGGCACGAG3'.

NS5B fl Reverse primer:
                                        (SEQ ID No 8)
5'TATGGATCCTTACCGGTTGGGGAGCAGG3'.
```

PCR cycles were: 96° C., 3 minutes, then 35 cycles of [94° C., 30 secondes/55° C., 30 secondes/72° C., 2 minutes], then 72° C., 7 minutes, then 4° C.

PCR amplified products were cloned into a yeast expression vector at XhoI/BamHI and XhoI/PstI sites to generate respectively the pVVS467 and pVVS468 constructs, which can express respectively a LexA DNA-binding domain-NS5B and a LexA DNA-binding domain-NS5B Δ 21 fusion protein in yeast. The bait plasmids constructed for the NS5B polymerase of Hepatitis C virus as a target protein. The full length NS5B is expressed as a fusion protein with the LexA-DBD or a mutated NS5B Δ 21 is expressed as a fusion protein with the LexA-DBD. The resulting plasmids are hereafter called bait-NS5B(fl) and bait-NS5B Δ 21.

2.3.2—Mutation of the leucine (L) residue in position 30 to Serine (S) has been shown to modify the conformation of NS5B protein (Labonté et al. 2002 JBC vol. 277 N041 pp 38838-38846). A mutant NS5B L30S is used to validate that the peptides are conformation sensitive peptides. Mutation L30S was introduced in pVVS467 and pVVS468 constructs according to the instructions QuickChange II XL Site-Directed mutagenesis kit of Stratagene. The primers used were:

```
Forward primer:
                                        (SEQ ID No 9)
5'AATCCGTTGAGCAACTCTTCGCTGCGTCACCAACAGTATG3'.

Reverse primer:
                                        (SEQ ID No 10)
5'CATACTGTGGTGACGCAGCGAAGAGTTGCTCAACGGA3'.
```

2.3—Bait Neuraminidase Expression Vector

Neuraminidase (NA) is a surface glycoprotein of 60 kd that has enzymatic activity essential for the replication of influenza A and B. The enzyme catalyses the cleavage of the α-ketosidic linkage that exists between a terminal sialic acid (N-acetyl neuraminic acid: NANA) and an adjacent sugar residue. This action has a number of important effects that enable the spread of the virus within the respiratory tract. These effects include the release of the virus from infected cells, the prevention of viral aggregates after release from host cells, the prevention of viral inactivation and the promotion of viral penetration into respiratory cells.

The neuraminidase was amplified by RT PCR from RNAs extracted from EB14 cells (VIVALIS, France) that had been previously infected by the influenza virus H1N1/PR8. RNAs were purified according to the instructions of Promega SV total RNA isolation kit. RNA was reverse transcribed according to Promega Random primers and AMV Reverse transcriptase kits' instructions. PCR amplification was realized using the primers with EcoRI and XhoI restriction sites:

```
Forward primer:
                                        (SEQ ID No 11)
5'CCAGAATTCCATTCAATTCAATTCAAACTGGAAG3'.

Reverse primer:
                                        (SEQ ID No 12)
5'ATACTCGAGCTACTTGTCAATGGTGAATGG3'.
```

PCR cycles were 96° C., 3 minutes, then 35 cycles of [94° C., 30 secondes/45° C., 30 secondes/68° C., 2 minutes], then 68° C., 7 minutes, then 4° C. The PCR amplified products were cloned into a yeast expression vector in EcoRI and XhoI sites to generate plasmid pVVS461 which express LexA-DNA-binding Domain-head/stalk domain of neuraminidase fusion protein in yeast.

2.4—Bait HIV P66 Expression Vector

HIV-1 RT is a heterodimer; the larger subunit, p66, is 560-amino-acids in length and contains both a polymerase and an RNaseH domain. The smaller subunit, p51, contains the first 440 amino-acids of p66 that correspond closely, but not exactly, to the polymerase domain. An essential element in the life cycle of this family of viruses is the requirement for integrating a copy of its genetic material (genome) into the human host cell genome before virus replication can occur. HIV RT is responsible for producing the DNA copy of the viral RNA genome that will be integrated into the human DNA.

A plasmid containing HIV-1 genome was used as templates to produce HIV p66 by PCR with the following oligonucleotides primers containing appropriate EcoRII and XhoI restriction sites:

```
Primer HIV P66-1 forward:
                                        (SEQ ID No 13)
5'ccagaattcattagccctattgagactgta3'.

Primer HIV P66-2 forward:
                                        (SEQ ID No 14)
5'ccagaattcgcagctgctgcagctgcacccattagccctattgagact
gta3'.

Primer HIV P66-3 forward:
                                        (SEQ ID No 15)
5'ccagaattccccattagccctattgagactgta3'.

Primer HIV P66 rev:
                                        (SEQ ID No 16)
5'ATACTCGAGTTATAGTACTTTCCTGATTCCAGC3'.
```

PCR cycles were: 96° C., 3 minutes, then 35 cycles of [94° C., 30 secondes/55° C., 30 secondes/72° C., 2 minutes], then 72° C., 7 minutes, and then 4° C.

PCR amplified products were cloned into a yeast expression vector at EcoRI/XhoI sites to generate the pVVS495-1, pVVS495-2, pVVS495-3 constructs.

Example 3

Expression Cassettes Used in Experiments with Mammalian Cells (e.g HeLa Cells)

Three different expression cassettes were used for the establishment of the screening of test compounds in Hela cells.

(A) Reporter expression cassette: The reporter expression cassette comprises a luciferase gene under the control of the inducible Gal4-upstream-activating sequences (Gal4-UAS), which include 5 repeats of the operator Gal4 17mer consensus sequence linked to a minimal mammalian promoter (eg. a synthetic TATA-box sequence, the minimal promoter of the human β-Globin gene or the minimal promoter of the HSV thymidine kinase gene). Other regulatory elements include the SV40 small T antigen splicing signals (intron) and polyadenylation signal (pA).

(B) Target protein expression cassette: The target protein expression cassette carries the target protein cDNA fused to the carboxy-terminus of the yeast Gal4 DBD under the control of the constitutive SV40 early promoter. Other regulatory elements include the beta-globin II splicing signals (intron) and SV40 polyadenylation signal (pA). Other constitutive eukaryotic promoters could be used such as the CMV promoter or the cellular EF1α promoter.

(C) Conformation sensitive peptide/VP16AD expression cassette: The conformation sensitive peptide/VP16AD expression cassette carries the selected conformation sensitive peptide fused to the carboxy-terminus of the viral VP16 activation domain under the control of the constitutive CMV promoter and enhancer. Other regulatory elements include a chimeric intron (5'-donor site from the first intron of the human beta-globin gene and the branch and 3'-acceptor site from the intron of an immunoglobulin gene heavy chain variable region) and SV40 polyadenylation signal (pA). Other constitutive promoter could be used instead of CMV promoter.

These three expression cassettes can be inserted into one, two or three different plasmids carrying additional selection genes to establish permanent cell lines. Among the available selection genes, Blasticidine and Puromycine resistant genes were selected for this study. Alternatively, the eukaryotic expression cassettes can be inserted in adenoviral vectors deleted in the E1 and E3 regions. After transfection of the recombinant DNA in complementation cell lines expressing the E1A and E1B products, virus production and lysis of the cells, the adenoviral particles are purified, titered and used to infect target cell lines at a multiplicity of infection allowing infection of 100% of the cells.

Example 4

Figure 3B:
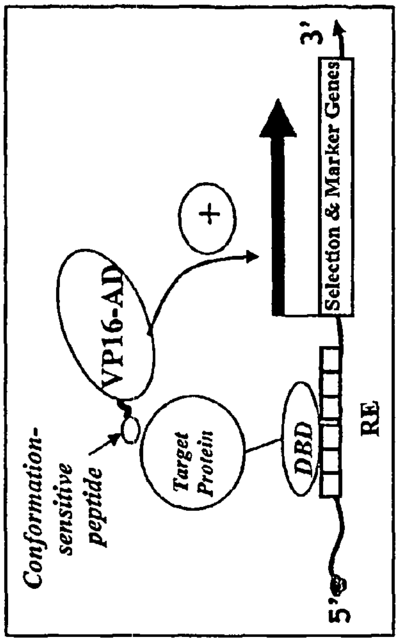
FIGS. 3A, 3B and 3C: Isolation of conformation sensitive peptides for a given target protein in the yeast two-hybrid-system A yeast strain is generated that carries a selection and marker gene whose expression is controlled by a target protein or a target protein ligand binding domain (LBD) linked to its own DNA binding domain (DBD) or to a heterologous DBD (eg. DBD of the procaryotic LexA protein). Expression of the selection gene is null in absence of ligands and no yeast would grow under selective pressure (FIG. 3A). Addition of a library of random peptides linked to the viral VP16 activation domain allows the identification of individual peptides ligands that specifically interact with the receptor and induce the expression of the selection gene through recruitment of the VP16 activation domain (FIG. 3B). Such peptides can easily be isolated from yeast colonies growing under selective conditions, then characterized and tested for their ability to bind to regions on the target protein that undergo conformational changes dependent on ligand binding. In presence of agonist or antagonist, conformational changes of the target protein prevent the binding of the conformation sensitive peptides and abolish selection gene expression (FIG. 3C).
Figure 3A:
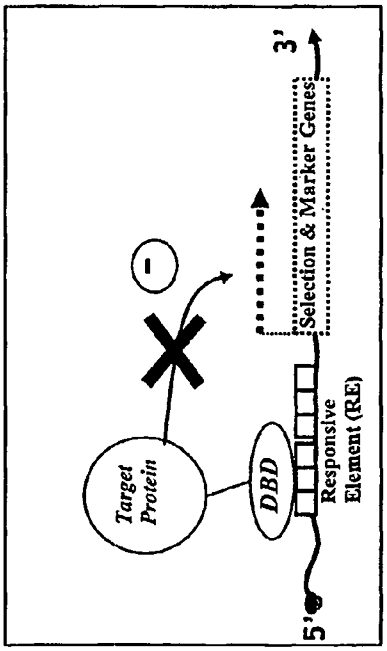
Figure 3C:
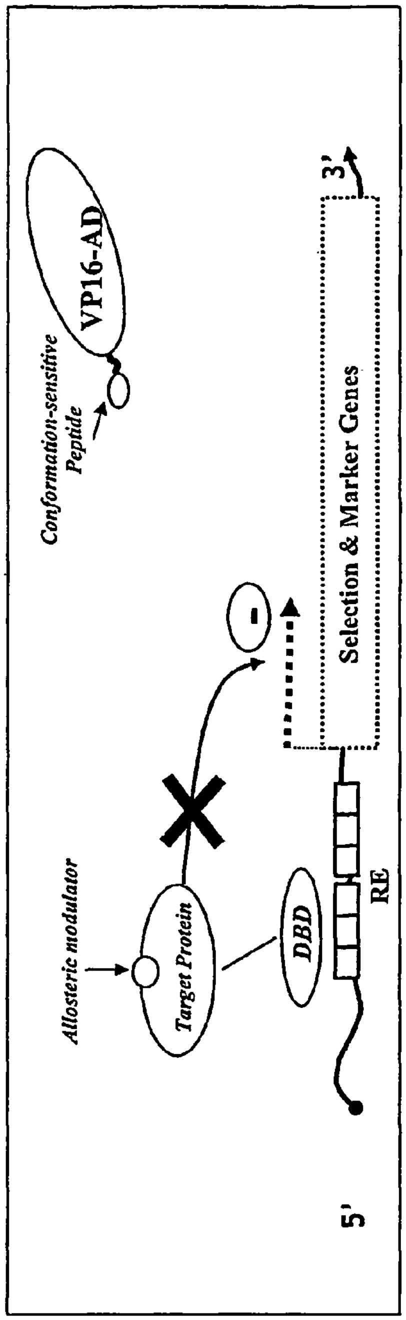

Identification of Conformation Sensitive Peptides with the Yeast Two-Hybrids Experiments Yeast two-hybrid experiments are carried out in the yeast strain (MATa; his3-Δ200; leu2-3,112; trp1-901; [plexAop]4::HIS3; [plexAop]8::lacZ), in which expression of the two reporter genes HIS3 and LacZ is under the control of the LexA operator sequence. This yeast strain cannot grow in absence of histidine in the culture medium, and yeast growth can be rescued only if expression of HIS3 gene is induced. Similarly, the LacZ reporter gene encoding the β-galactosidase marker is not expressed in this yeast strain. The bait plasmids encoding either the full-length or a region of the target protein (Nuclear Receptor, viral proteins for example), and the random peptide/VP16-AD library were transformed into the yeast strain and yeast colonies growing in absence of histidine were selected. Only yeast colonies in which a strong interaction between the bait (i.e. NR, viral proteins, . . . ) and the prey (peptide-VP16-AD) proteins did occur would grow under such selective culture conditions and will express the LacZ reporter gene (FIG. 3). Growth of false positive clones may be prevented by adding 3-amino-triazole (3AT), a competitive inhibitor of HIS3, to the medium. Addition of ligand (agonist or antagonist) to the medium shall suppress the growth of some clones, indicating that a conformation sensitive peptide/VP16-AD protein is dissociated from the target protein (i.e. NR, viral proteins), as a probable consequence of ligand-induced target protein-conformational changes, resulting in a shut-off of HIS3 and lacZ genes expression. All conformation sensitive peptides dissociated by both target protein agonists and antagonists were selected for further characterization with the aim to develop screening platforms that allow the search of both activators and inhibitors of target protein in one single assay. The biological activity of each isolated conformation sensitive peptide is reconfirmed by isolation of conformation sensitive peptide encoding plasmids, re-transformation into yeast strain and analysis of HIS3 and lacZ gene expression in absence of histidine and in presence of target protein or non-target protein ligands in a spot test, as well as in a quantitative LacZ assay.

Figures 4A, 4B, 4C:
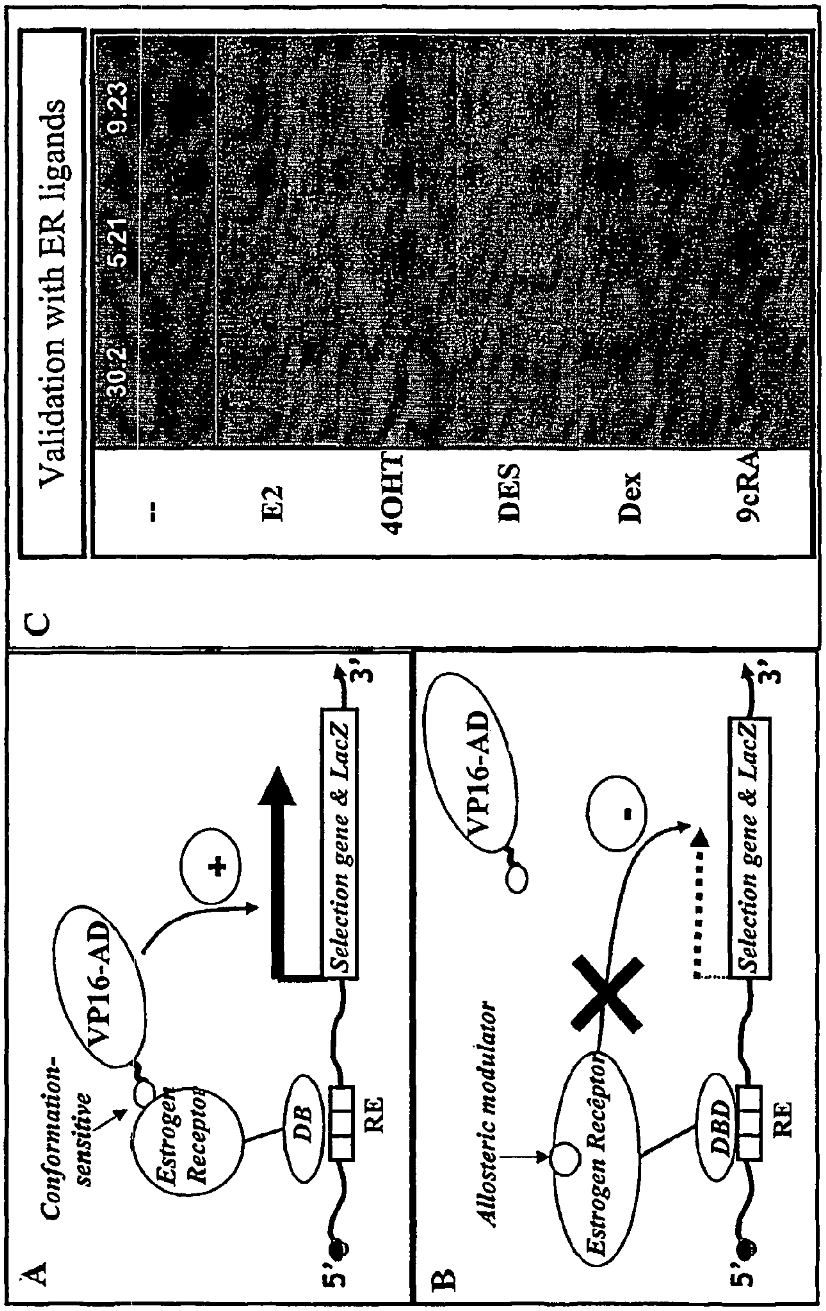
FIGS. 4A, 4B and 4C: Characterization of ERα conformation sensitive peptides in a spot test Yeast strain (MATa; his3-Δ200; leu2-3,112; trp1-901; [plexAop]4::HIS3; [plexAop]8::lacZ) were transformed by vectors expressing the ERα-DEF bait and peptides-VP16AD interacting with the un-liganded form (peptides: 30-2; 5-21; 9-23) are spotted on selective medium lacking histidine, leucine and tryptophane (left panel), supplemented with ER ligands (agonists: estradiol (E2) and diethylstilbestrol (DES) or antagonist: 4-hydroxy-tamoxifen (4OHT)) or with non-ER ligands (9cis-retinoic acid (9-cRA), dexaméthasone(Dex)) or in absence of any ligand. Reporter genes (His3 and LacZ) are expressed upon interaction between the peptides and ER in the un-liganded form (clones are growing under selective conditions and stain positive for lacZ). Addition of ER ligands induces conformational changes of the receptor, and 3D-sensor peptides are dissociated from the liganded form (clones are not growing under selective conditions). The 3D-sensor peptides are not dissociated from ER in the presence of non-ER ligands that do not bind to ERα (all clones are growing under selective conditions and stain positive for lacZ).

4.1—Identification in Yeast of Conformation Sensitive Peptides Interacting with the Estrogen Receptor The bait plasmids encoding the full length or the DEF regions of the ERα and the prey peptide/VP16-AD VV01 library (diversity of $6.10^7$) were transformed into the yeast strain. Yeast colonies growing in absence of histidine were selected. Only yeast colonies in which a strong interaction between the bait (ERα) and the prey (peptide-VP16AD) proteins did occur would grow under such selective culture conditions and express the LacZ reporter gene. Growth of false positive clones was prevented by adding 3-amino-triazole (3AT), a competitive inhibitor of HIS3 to the medium. A total of 484 colonies and 109 colonies were isolated for the bait-ER (DEF) and for the bait-ER (fl) screening experiments, respectively. Out of the 484 clones, 40 were randomly picked for further studies. FIG. 4 (left panel) shows the growth and LacZ-expression of 3 individual yeast clones in absence of histidine in the culture medium either with ER ligands or with non-ER ligands or in absence of any ligand. Addition of estradiol (E2), 4-hydroxytamoxifen (4OHT) and diethylstilbestrol (DES) to the medium suppresses the growth of most clones, indicating that the conformation sensitive peptide/VP16AD protein is dissociated from ERα, as a probable consequence of hormone-induced ERα-conformational changes, resulting in a shut-off of HIS3 and lacZ genes expression. In contrast, addition of dexamethasone, a ligand for the glucocorticoid receptor (not shown), or 9-cis retinoic acid (9cRA), a ligand for the retinoic acid receptor, had no effect on these yeast clones. These data show that most yeast clones contain peptide sequences that can interact to ERα and also "sense" specific ERα conformational changes that are induced upon agonist (E2) or antagonist (4OHT) binding. Similar results have been found with another agonist (diethylstilbestrol: DES).

In summary, these experiments revealed four classes of peptide binders also named "3D-screen" peptide:

- peptides dissociated by addition of both agonists (E2, DES) and antagonists (4OHT);
- peptides dissociated by addition of E2 only;
- peptides dissociated by addition of 4OHT only;
- peptides dissociated by addition of 4OHT, but whose binding to ERα was increased upon addition of E2.

All 3D-screen peptides dissociated by both ER agonists and antagonists were selected for further characterization with the aim to develop screening platforms that allow the search of both activators and inhibitors of ERα in one single assay. The biological activity of each isolated 3D-Screen peptide was reconfirmed by isolation of 3D-Screen encoding plasmids, retransformation into the yeast strain (MATa; his3-Δ200; leu2-3,112; trp1-901; [plexAop]4::HIS3; [plexAop]8::lacZ) and analysis of HIS3 and lacZ gene expression in absence of Histidine and in presence of ER or non-ER ligands in a spot test.

Clones 5-21, 9-23 and 30-2 were thereafter selected as containing the most potent 31)-screen peptides able to "sense" ERα conformational changes induced by both agonist and antagonist ligands (FIG. 5). The sequence of the selected 3D-screen peptides able to "sense" ERα conformational changes induced by both agonist and antagonist ligands are:

ERα 3D-screen peptide 5-21:
S C C T Q H V C Y R P R A Y R (SEQ ID No 17)

ERα 3D-screen peptide 9-23:
S I T T L F Y H A M F G F V P (SEQ ID No 18)

ERα 3D-screen peptide 30-2:
F C T P I R M F Y R A P L W D L N K. (SEQ ID No 19)

These clones were selected for confirmation in mammalian cells for their usefulness in small molecule libraries screening.

4.2—Identification in Yeast of Conformation Sensitive Peptides Interacting with RARα

Similarly to ERα, yeast two-hybrid experiments were carried out for the human retinoic acid receptor alpha (RARα) to identify peptides that sense the conformational state of the receptor with the ultimate goal to use such 3D-screen peptides as a tool to identify novel small molecules.

The bait plasmids encoding either the full-length or the DEF regions of RARα and the prey peptide/VP16-AD VV01 library (diversity of $6.10^7$) were transformed into the yeast strain (MATa; his3-Δ200; leu2-3,112; trp1-901; [plexAop]4::HIS3; [plexAop]8::lacZ) and yeast colonies growing in absence of histidine were selected. Only yeast colonies in which a strong interaction between the bait RARα and the prey peptide/VP16-AD proteins did occur would grow under such selective culture conditions and express the lacZ reporter gene. Growth of false positive clones was prevented by adding 3-amino-triazole (3AT).

Figures 6A, 6B, 6C:
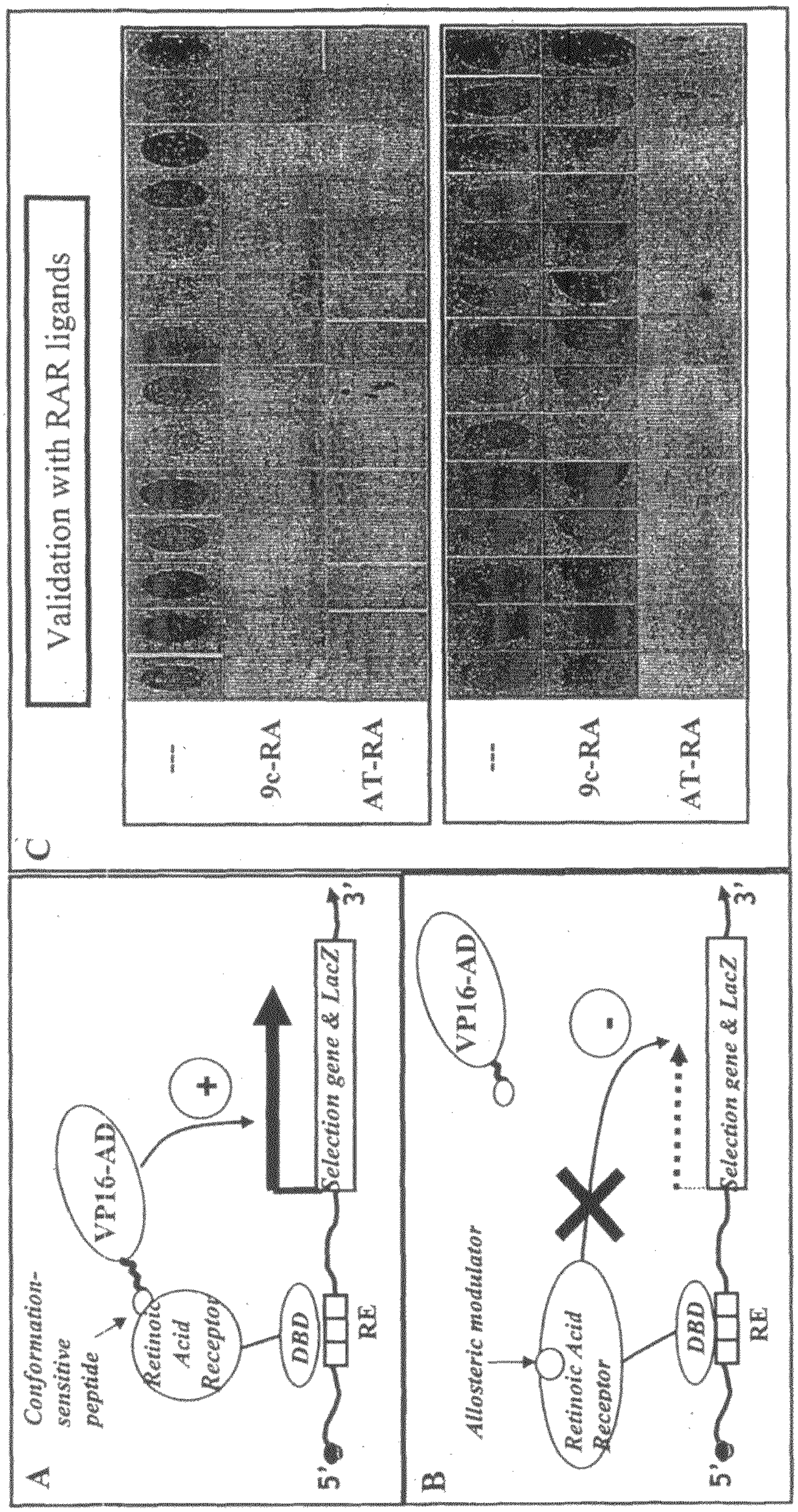
FIGS. 6A, 6B and 6C: Characterization of RARα 3D-conformation sensitive peptides in spot assays Yeast strain (MATa; his3-Δ200; leu2-3,112; trp1-901; [plexAop]4::HIS3; [plexAop]8::lacZ) were transformed by vectors expressing the RARα-DEF bait and peptides-VP16AD interacting with the un-liganded form (28 peptides were identified) are spotted on selective medium lacking histidine, leucine and tryptophane (left panel), supplemented with RARα ligands (9c-RA and all-trans Retinoic acid (AT-RA)) or in absence of any ligand. Reporter genes (His3 and LacZ) are expressed upon interaction between the peptides and RARα in the un-liganded form (clones are growing under selective conditions and stain positive for lacZ). Left upper panel represents 18 yeast clones containing peptides sensitive to RARα conformational changes induced by 9C-RA and AT-RA. Left lower panel represents 18 clones containing peptides sensitive to RARα conformational changes induced by only AT-RA.

Several hundred clones were isolated using RAR-DEF- or RAR-fl as bait proteins. 270 individual clones containing peptide/VP16AD binders for RAR-DEF were randomly picked for further analysis. FIG. 6 shows as a representative example the growth and LacZ expression of 28 selected clones in absence of histidine and RARα ligands (left panel). Addition of 9-cis-Retinoic Acid (9c-RA) A or all-trans-Retinoic Acid (AT-RA) suppresses the growth of 14 of these clones (upper panel) indicating that the peptide/VP16AD protein is dissociated from the receptor, as a consequence of the ligand-induced conformational changes, resulting in a shut-off of HIS3 and lacZ expression. On the lower panel are 14 other selected clones that show a selective dissociation of the peptide/VP16AD protein induced only by the AT-RA ligand. The selected peptides are therefore 3D-Screen peptides that can interact specifically with the un-liganded RARα and “sense” subtle RARα conformations that are induced upon RAR ligand addition.

In summary, 4 classes of RARα 3D-screen peptides were identified (Table II), dissociated either by 9c-RA or AT-RA or both, or for which the reporter gene expression is up-regulated in the presence of both ligands:

TABLE II

Analysis of RARα 3D-sensor peptides

| Ligand effect | Nb clones/270 | % |
|---|---|---|
| Inhibition by AT-RA & 9c-RA | 38 | 14 |
| Inhibition by AT-RA | 33 | 12 |
| Inhibition by 9c-RA | 1 | 0.4 |
| Induction by 9c-RA & AT-RA | 38 | 14 |
| No effect | 157 | 58 |

FIG. 7 shows the amino-acid sequence of four 3D-Screen peptides whose interaction with RARα is prevented by either or both AT-RA and 9c-RA:

```
RARα 3D-screen peptide I-B8:
M P A D I L F A N P Q C R I N         (SEQ ID No 20)

RARα 3D-screen peptide I-C8:
A P F P V V Y W S D W C N Q Q         (SEQ ID No 21)

RARα 3D-screen peptide III-D2:
W V V Y A S L C F K A C Y F G L N K  (SEQ ID No 22)

RARα 3D-screen peptide II-F8
A T L E W R L F T R F I T W G L I P  (SEQ ID No 23)
L E
```

The most potent 3D-screen peptides have been selected for the development of a human cell screening platform to search novel small molecules inducing specific conformational changes and modulating the RARα activity.

4.3—Identification in Yeast of Conformation Sensitive Peptides Interacting with the NS5B Protein of HCV Similarly to ERα and RARα, yeast two-hybrid experiments were carried out for the NS5B protein of Hepatitis C virus to identify peptides that sense the conformational state of the polymerase with the ultimate goal to use such 3D-screen peptides as a tool to identify novel anti-viral molecules.

Yeast two-hybrid experiments were carried out in the yeast strain (MATa; his3-Δ200; leu2-3,112; trp1-901; [plexAop]4::HIS3; [plexAop]8::lacZ) transformed with the RNA dependent RNA polymerase of HCV deleted of the last 21 C terminus residues, NS5BΔ21 fused to the LexA-DBD as a bait and the VV01 peptide library as a prey. The C terminal 21 residues of HCV NS5B correspond to a very hydrophobic sequence supposed to support the membrane-anchoring domain of the protein. Only colonies in which an interaction between NS5BΔ21-LBD and a peptide—VP16 occurs can grow in the absence of Histidine.

Figures 8A, 8B, 8C:
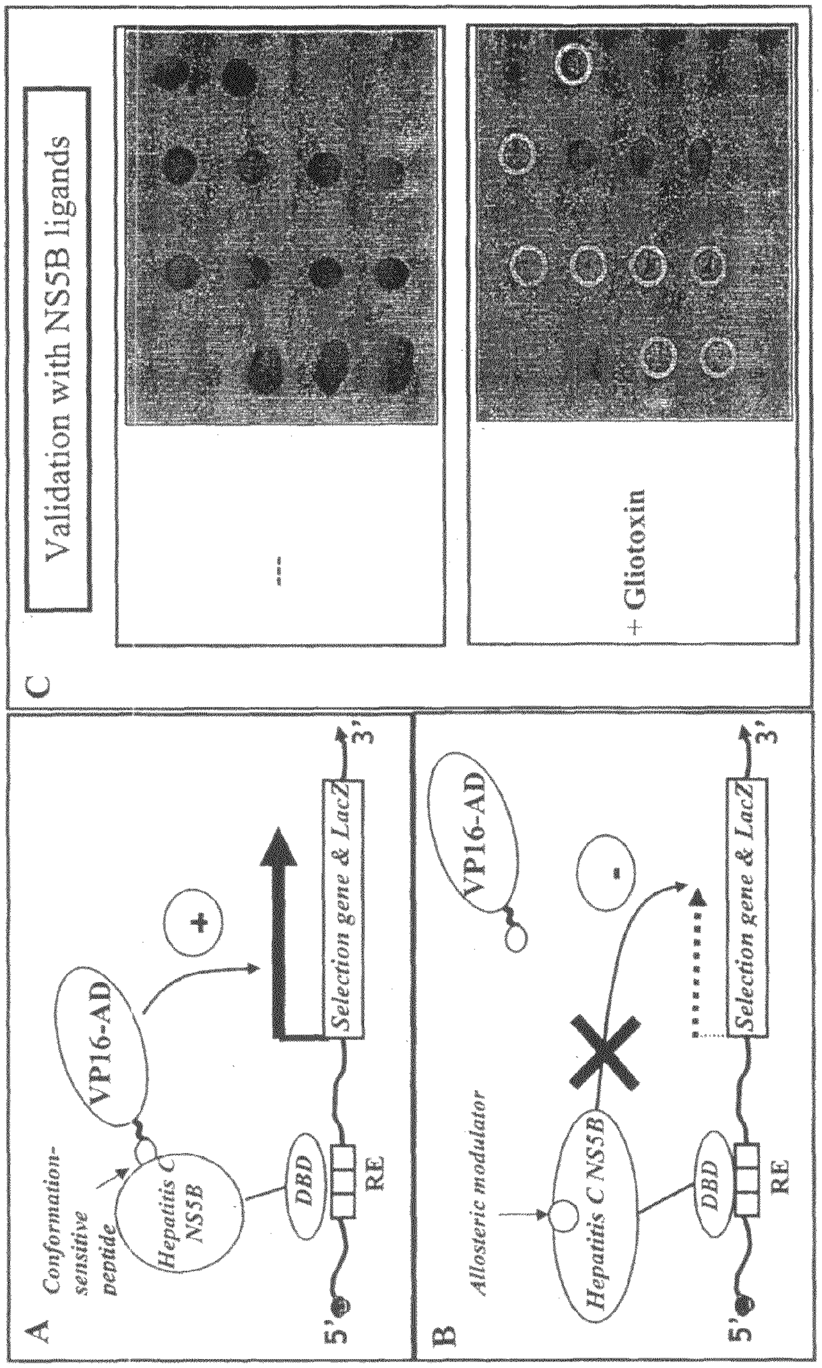
FIGS. 8A, 8B and 8C: Characterization of HCV polymerase NS5B conformation sensitive peptides in spot assays Yeast strain (MATa; his3-Δ200; leu2-3,112; trp1-901; [plexAop]4::HIS3; [plexAop]8::lacZ) were transformed by vectors expressing the RARα-DEF bait and peptides-VP16AD interacting with the un-liganded form are spotted on selective medium lacking histidine, leucine and tryptophane (left panel), supplemented with gliotoxin or in absence of gliotoxin. Reporter genes (His3 and LacZ) are expressed upon interaction between the peptides and NS5B in the un-liganded form (clones are growing under selective conditions and stain positive for lacZ). Left upper panel represents 13 yeast clones containing peptides binding to NC5B in absence of gliotoxin. Left lower panel shows 8/13 clones containing peptides sensitive to NC5B conformational changes induced by gliotoxin.

768 colonies were isolated and grown on selective medium without Histidine supplemented with 20 μM Gliotoxin (Rodriguez et al., 1992, J. Virol. 66(4), pp 1971-1976). In the absence of gliotoxin, peptides interact with NS5B and stain positive for LacZ expression (FIG. 8, left panel). Addition of gliotoxin to the medium induces specific conformational changes of NS5B, leading to the dissociation of the conformation sensitive peptides from the polymerase. The result is a shut-off of HIS3 and the prevention of growth of the yeast, and a shut-off of LacZ gene expression (FIG. 8, lower panel).

In contrast addition of nucleoside substrate analogue, as ribavirin, that does not induce conformational change of NS5B, has no effect on yeast growth.

Of 768 colonies screened, 75 colonies were obtained that contained peptides sensitive to the conformation of NS5B.

Example 5

Generation of HeLa Cells Screening Platform

The three expression cassettes described before (example 3) were inserted into one, two or three plasmids carrying additional selection genes to establish human permanent cell lines. Among the available selection genes, Blasticidine and Puromycine resistant genes were selected for this study.

5.1—Cells:

HeLa cells, which are derived from a human cervical carcinoma, will be selected for the described experiments, but any others mammalian cell can be used for the generation of the conformation sensitive peptides human cell screening platform.

5.2—Transient Transfections of the Expression Plasmids:

HeLa cells were transiently transfected with the plasmid using the optimized jetPEI transfection protocol (PolyPlus Transfection, Illkirch, France).

Target protein ligands were added to the cell culture medium 24 hours after transfection. According to a better embodiment of the invention the target protein ligand is a small chemical molecule. Luciferase activity is measured 24 hours later.

Figures 9A, 9B:
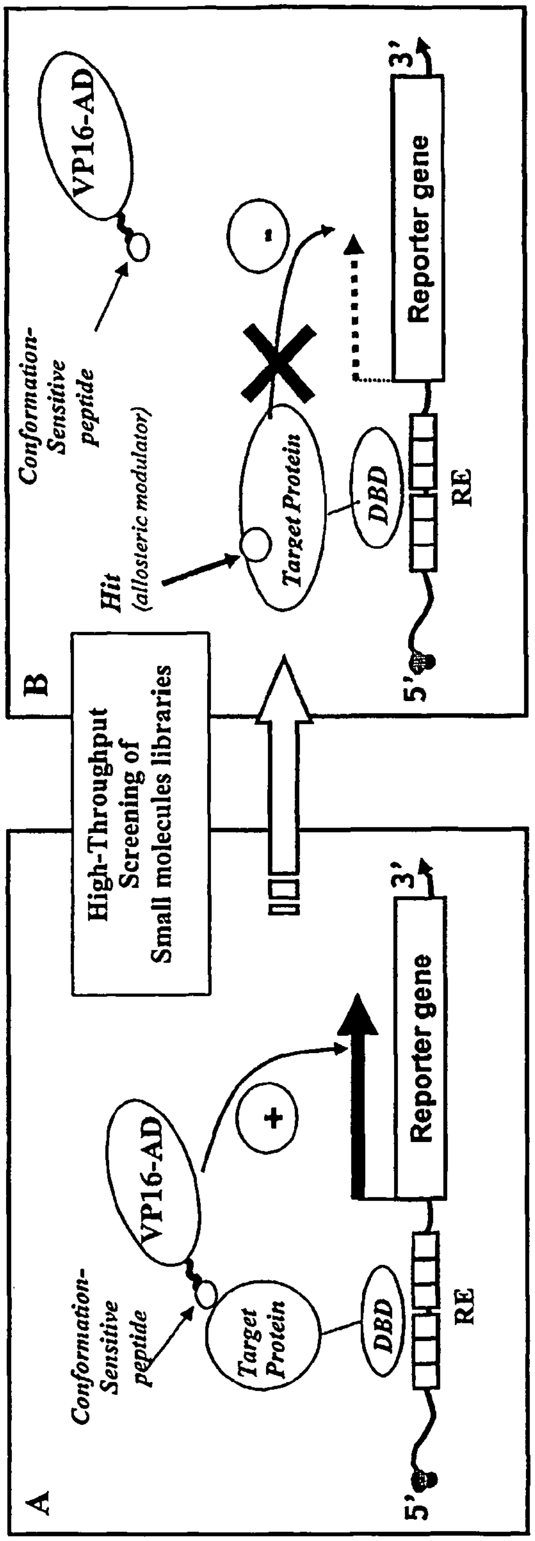
FIGS. 9A and 9B: High throughput screening of small molecule library for chemical hits altering the target protein (i.e ERα) conformation FIG. 9A. Interaction of the conformation sensitive peptide with the target protein in the unliganded state (native conformation): human cells will be transfected with three expression plasmids encoding the reporter gene (eg. Luciferase), the target protein fused to a DNA, Binding Domain (DBD) and the conformation sensitive peptide previously screened in yeast and fused to the VP16-AD, respectively. Expression of the reporter gene will be strongly induced upon recruitment of the conformation sensitive-peptide/VP16-AD protein to the target protein already bound to the DNA response elements (RE) upstream of the reporter gene.
Figure 10:
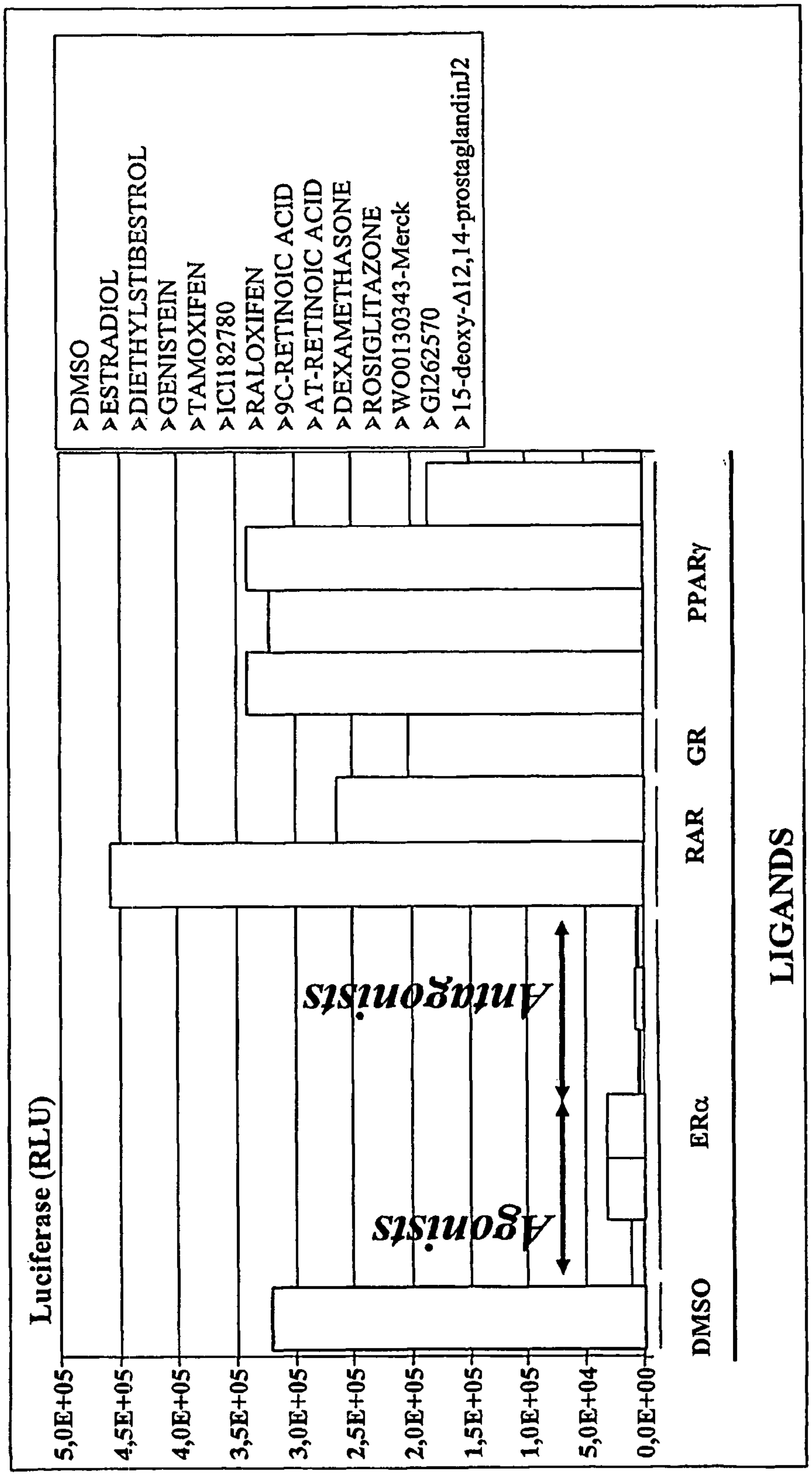
FIG. 10: Generation of a 3D-screen human cell screening platform for ERα Hela cells are transiently transfected with three expression plasmids encoding the reporter gene luciferase (eg. UAS-Luc), the target protein fused to a DNA Binding Domain (DBD) and the conformation sensitive peptide previously screened in yeast and fused to the VP16-AD, respectively with the jetPEI reagent. This cell lines carries then the confirmation sensitive peptide for the estrogen receptor alpha (ERα) and the luciferase reporter gene whose expression is controlled by the ERα/3D-Sensor complex. This platform was used to screen a small molecule library. Expression of luciferase is strong in absence of ligand or when ligands for unrelated nuclear receptors (non-ER ligands) are added. In contrast, luciferase expression is abolished when ERα ligands (agonists and antagonists) are tested. Screening of the library allows the rapid identification of many hits that specifically modulate the receptor conformation and prevent luciferase expression (examples of hits: E3, A8, E7, C8, D9, B9, A9).

Co-transfection of the reporter (UAS-Luc), target protein and conformation sensitive peptide-VP16AD expression plasmids into HeLa cells lead to a strong activation of luciferase activity in the absence of small molecule ligands. This confirms that the conformation sensitive peptide/VP16AD protein is also effective in human cells. In contrast, luciferase expression is strongly reduced upon addition of target protein agonist or antagonist. The conformation sensitive peptide is not able to interact with a target protein that has undergone conformational changes upon ligand binding. Moreover, the luciferase expression is not inhibited upon addition of ligands for unrelated target proteins (negative control) (FIG. 9).

Such conditions are therefore used to screen small molecule libraries and search for novel chemical compounds that induce conformational changes of the target protein.

5.3—Screening of Small Molecules Library for Hits Modulating ERα Conformations 53.1—Transient Transfections of the Expression Plasmid HeLa cells were transiently transfected with plasmid using the optimized jetPEI transfection protocol (PolyPlus Transfection, Illkirch, France). Briefly, cells are seeded in 24-well plates at a density of $7.5\times10^4$ cells per well and 1 μg of total DNA is complexed to jetPEI at an N/P ratio of 8 (number of nitrogen residues of jetPEI per DNA phosphate residues). The optimal ratio between the reporter, ER and 3D-Screen plasmids was: 300 ng reporter plasmid (UAS-Luc), 100 ng ER expressing plasmid and 50 ng peptide plasmid (ERα 3D screen peptide N° 5-21), complemented to 1 μg with a neutral carrier DNA. Chemical ligands are added to the cell culture medium 24H after transfection. Luciferase activity was measured 24H later. A slightly modified experimental protocol was used to screen small molecule libraries: $10^6$ cells are transfected in 10 cm-diameter dishes with 10 μg of total DNA complexed to jetPEI at an N/P ratio of 8. Cells are trypsinised and plated in 96 well-plates (or 384 well-plates) at $5\times10^4$ cells per well 24H after transfection, and small molecules are added upon cell adhesion. Luciferase activity is measured 24 H later.

Figure 11:
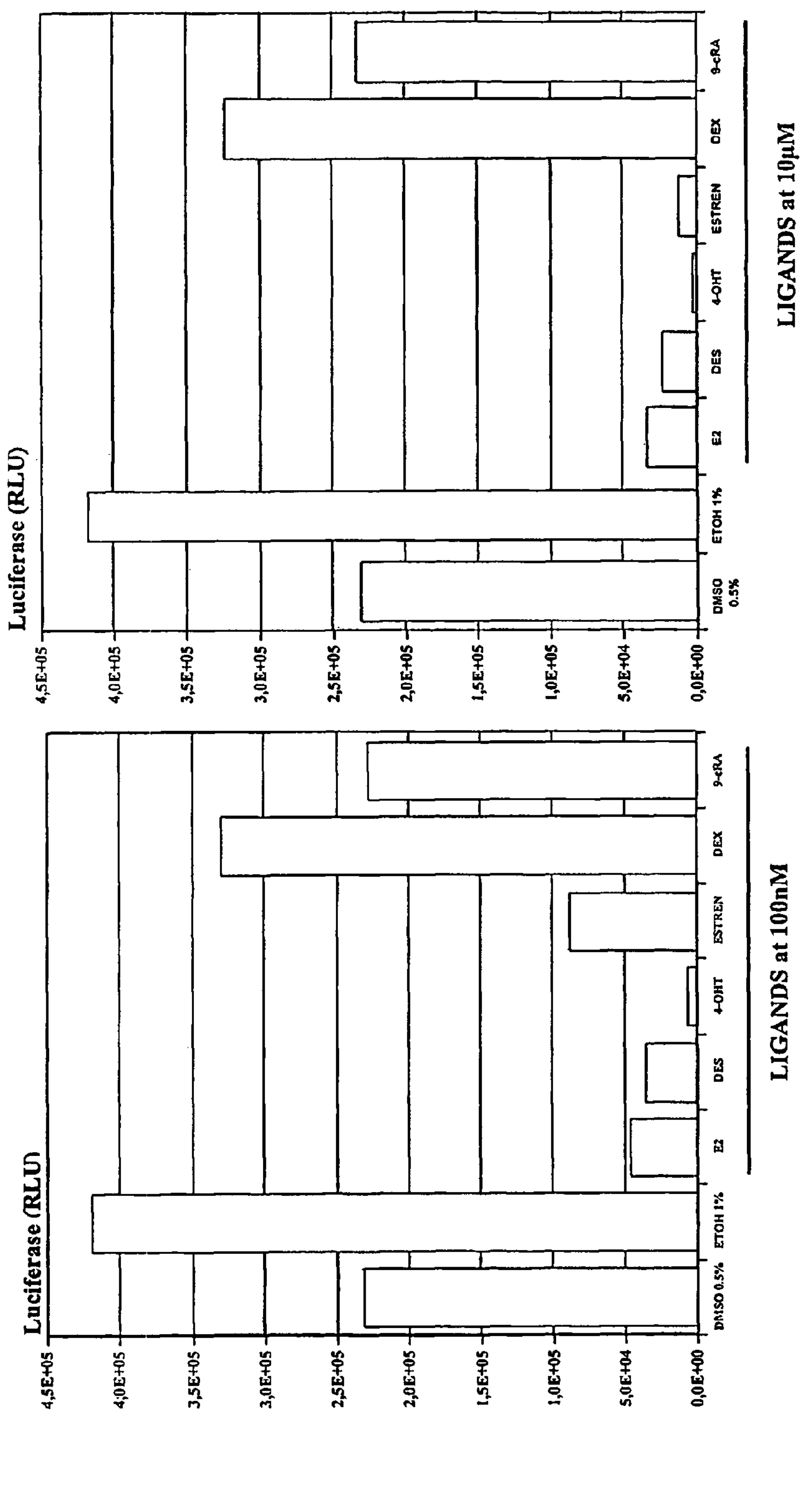
FIG. 11: Identification of Estren with the 3D-screen human cell screening platform for ERα

As expected, co-transfection of the reporter (UAS-Luc), ERα and 3D-Screen-VP16AD expression plasmids into HeLa cells led to a strong activation of luciferase activity in the absence of small molecule ligands (FIGS. 11, 12 and 13), confirming that the selected 3D-screen/VP16AD protein is also effective in human cells. In contrast, luciferase expression is strongly reduced upon addition of ER agonist or antagonist (E2, DES, GEN, 4OHT, ICI, RAL; (FIGS. 11, 12 and 13). The 3D-screen peptide is thus not able to interact with a receptor that has undergone conformational changes upon ligand binding. Finally, luciferase expression is not inhibited upon addition of ligands for unrelated nuclear receptors (non-ER ligands; (FIGS. 11 and 12). Such conditions can therefore be used to screen small molecule libraries and search for novel chemical compounds that induce conformational changes of the target NR. Similar results were obtained with two independent ERα 3D-Screen peptides (# 9-23 & 30-2) by using 1 or 10 μM of ligand, together with either the full-length ERα or the ERα DEF regions.

Of note, the fact that the Gal4-ER(fl) fusion protein remains inactive even after of ER agonists is an important since: i) background luciferase activity is minimal in the absence of ligand or in the presence of ER ligands; ii) luciferase expression is strongly induced upon interaction of the un-liganded ER with the 3D-screen/VP16AD protein; iii) luciferase expression is strongly reduced in presence of ER ligands only, as well agonists as antagonists, as a consequence of the dissociation between the 3D-sensor/VP16AD and the liganded receptor.

5.3.2—Screening of a Small Molecule Library for Hits Modulating the ERα Conformations (FIG. 13)

A small molecule library of 13280 original chemical compounds was screened in HeLa cells under the experimental conditions described above. The three expression plasmids, UAS-luc, full-length ER and 3D-screen/VP16AD (#30-2) were co-transfected in Hela cells in large dishes. Cells were then reseeded in a 96-well plate format 24 H after transfection and chemical compounds are added upon cell adhesion. Luciferase activity was measured 24 H later. Internal controls were also included, consisting in known ER- or non-ER ligands as previously indicated. Under these conditions, around 100 small molecule hits were identified that specifically modulate the receptor conformation and prevent luciferase expression (luciferase expression reduced over 90%). FIG. 13 shows the results from 160 compounds. β-estradiol (#55-A9), estriol (#55-B9) and diethylstilbestrol (#55-C8), all ER ligands, were among the 7 hits shown in this figure, validating the 3D-Sensor screening platform. Several novel hits inducing conformational changes of ER could indeed be identified with this technology.

All the hits identified during the primary screening were confirmed in a second set of transfections in Hela cells, either by co-transfection of the UAS-Luc and 3D-screen/VP16AD plasmids together with plasmids ER-fl or ER-DEF). All chemical compounds identified in the primary screening were confirmed to effectively dissociate the interaction of the 3D-screen peptide from both the full-length and DEF forms of ERα.

Furthermore, the potential agonist and antagonist properties of these hits were investigated in HeLa cells by co-transfection of an ERE-luc reporter plasmid, in which the luciferase gene is under the control of the estrogen-responsive elements (ERE), and an expression plasmid encoding the wild-type ERα. Transfections were performed as previously described for the primary screening, and cells are inclubated for 24 H either in the presence of the chemical hits alone to test for their agonist activity, or in the presence of the hit together with 100 nM E2 to test for their antagonist activity. As an example of results obtained with 28 representative hits, we identified 15 hits, among which 6 and 9 were found to display agonist and antagonist properties, respectively. Interestingly, the 13 other hits are therefore inducing ERα to change its conformation, but without any obvious effect on its transcriptional activity, at least in HeLa cells. Such compounds are hits that could not be identified otherwise using classical screening systems and may display unexpected biological properties in other cell systems or tissues (FIG. 14). Estren, a synthetic molecule that cannot be detected using classical screening assays, was included in the assay to determine whether this novel screening platform can allow the isolation of such molecule (FIG. 12). As expected, Estern is very effectively detected with the 3D screen sensor technology inducating that this molecule does induce a conformational change to the receptor. Estren was demonstrated to prevent apoptosis of bone cells without affecting the reproductive organs, so without the side effects of molecules used to treat osteoporosis (Science, 298, 2002, p 843).

The invention claimed is:

1. A method of selecting test compounds having the ability to modulate the biological activity of a target protein by modifying the conformation of said target protein, said method consisting essentially of:

A) providing a combinatorial library of peptides, wherein said library is expressed in a plurality of yeast cells and said cells collectively express all members of said library, and wherein each cell co-expresses said target protein or a ligand-binding protein moiety thereof and one member of said library; and wherein each cell further comprises a signal producing system comprising:

a protein-bound component which is fused to said target protein or to said ligand-binding protein moiety thereof, so as to provide a chimeric protein; and a peptide-bound component which is fused to said peptide so as to provide a chimeric peptide, where one of said components is a DNA-binding domain (DBD) and the other component is a complementary transactivation domain (AD), and the signal producing system further comprises at least one reporter gene operably linked to an operator bound by said DBD, the binding of the peptide to the target protein or protein-binding moiety thereof resulting in the constitution of a functional transactivation activator protein which activates expression of said reporter gene and a signal is produced by activation of the expression of a reporter gene when the peptide-bound and protein-bound components are brought into physical proximity as a result of the binding of the peptide to said target protein or moiety thereof;

B) screening said library for the ability of its members to bind said target protein in a native conformation and selecting the peptides binding to said target protein in native-conformation;

C) providing a known ligand of said target protein, wherein the binding of said known ligand to the target protein induces a conformational change in said target protein;

screening the peptides selection selected in B) and selecting among the peptides selected in B) those having a decreased or no ability to bind to said target protein in presence of said known ligand compared to the ability of said peptides to bind to said target protein in native conformation;

wherein step C) is further carried out with at least another known ligand; and wherein a conformation-sensitive peptide is selected for having a decreased or no ability to bind to said target protein in presence of the known ligands compared to the ability of said conformation-sensitive peptide to bind to said target protein in native conformation, said conformation-sensitive peptide thereby presenting the ability to identify conformational changes induced by more than one known ligand; and D) screening a library of test compounds in a human cell line for their ability to alter the binding of a single conformation-sensitive peptide of those selected in step C) to said target protein in native conformation; and selecting among said library of test compounds those test compound(s) that alter the binding of said single conformation- sensitive peptide, wherein the presence of said test compound(s) results in a decrease or an absence of binding of said single conformation-sensitive peptide to the target protein;

and wherein said cell line in step D) co-expresses:

a) said target protein, or a ligand-binding protein moiety thereof, and b) said single conformation-sensitive peptide selected in step C); said cell further comprising a signal producing system comprising:

a protein-bound component which is fused to said target protein or to said ligand-binding protein moiety thereof, so as to provide a chimeric protein; and a peptide-bound component which is fused to said peptide so as to provide a chimeric peptide, wherein one of said components is a DNA-binding domain (DBD) and the other component is a complementary transactivation domain (AD), and the signal producing system further comprises at least one reporter gene operably linked to an operator bound by said DBD, the binding of the peptide to the target protein or protein-binding moiety thereof resulting in the constitution of a functional transactivation activator protein which activates expression of said reporter gene and a signal is produced by activation of the expression of a reporter gene when the peptide-bound and protein-bound components are brought into physical proximity as a result of the binding of the peptide to said target protein or moiety thereof.

2. The method of claim 1 wherein the library of test compounds comprises between 1 to 10 millions of compounds.

3. The method of claim 1 in which the test compound is endogenously or, preferably, exogenously added to the cell of step D.

4. The method of claim 1 wherein (i) the peptide-bound component which is fused to said peptide to provide a chimeric peptide is a complementary transactivation domain (AD); and (ii) the protein-bound component which is fused to said target protein to provide a chimeric protein is a DNA-binding domain (DBD).

5. The method of claim 4 where the DBD is selected from the group consisting of Gal4 and LexA and where the AD is selected from the group consisting of *E. coli* B42, Gal4 activation domain II, and HSV VP16.

6. The method according to claim 1 wherein said cell used in steps D) and E) to perform the screening and the selection of the test compound(s) is a HeLa cell.

7. The method according to claim 6 wherein the following three different expression cassettes are used for the establishment of the screening of the test compounds in the HeLa cells:

a reporter expression cassette comprising a luciferase gene under the control of the inducible Gal4-upstream-activating sequences (Gal4-UAS);

a target protein expression cassette carrying the target protein cDNA fused to the carboxy-terminus of the yeast Gal4 DBD under the control of the constitutive SV40 early promoter; and a conformation sensitive peptideNP16AD expression cassette carrying the selected conformation sensitive peptide fused to the carboxy-terminus of the viral VP16 activation domain under the control of the constitutive CMV promoter and enhancer.

8. The method of claim 1 wherein the target protein is a hepatitis C virus protein selected among protease NS2/3, serine protease NS3-4A, NS3 RNA helicase, cofactor UA, cofactor UB, RNA polymerase 5B, and non-structural protein 5A.

9. The method of claim 8 wherein when the target protein is a hepatitis C viral protein selected among:

a) NS3-4a serine protease, then the known ligand is selected among pyrrolidine-5,5-translactam, derivatives of 2,4,6-trihydroxy-3-nitro-benzamides, thiazolidines, benzanilides, BILN2061; and b) NS3 RNA helicase, then the known ligand is selected among 2,3,5-trisubstituted-1,2,4-thiadiazol-2-ium salts; and c) other hepatitis C viral proteins, then, the known ligand is selected among ribavirin, levovirin, viramidine, merimpodib, thymosin alpha 1, amantadine.

10. The method of claim 1 wherein the target protein is an influenza virus protein selected among neuraminidase, protein M2 and haemagglutinin.

11. The method of claim 10 wherein when the target protein is an influenza virus viral protein selected among:

a) neuraminidase, then the known ligand is selected among zanamivir and oseltamivir, and b) protein M2, then the known ligand is selected among amantadine and rimantadine.

12. The method of claim 1 wherein the target protein is a lentiviral protein selected among integrase, protease, TAT, NEF, REV, VIF, Vpu, Vpr.

13. The method of claim 12 wherein when the target protein is an HIV viral protein selected among:

a) viral protease, then the known ligand is selected among amprenavir, indinavir, saquinavir, lopinavir, fosamprenavir, ritonavir, atazanavir, nelfinavir; and b) reverse transcriptase, then the known ligand is selected among lamivudine, zalcitabine, delavirdine, zidovuline, efavirenz, didanosine, nevirapine, tenofovir disoproxil fumarate, abacavir, stavudine.

14. The method of claim 1 where said target protein is a human nuclear receptor selected among an estrogen receptor, an androgen receptor, a glucocorticoid receptor, a retinoic acid receptor alpha (RARα), a retinoic X receptor (RXR), a peroxisome proliferators-activated receptor (PPARs), a liver X receptor alpha (LXRα).

15. The method of claim 1 wherein when the target protein is a nuclear receptor selected among:

a) estrogen receptor, then the known ligand is selected among: estradiol, diethylstilbestrol, genistein, tamoxifen, ICI182780, raloxifen; and b) androgen receptor, then the known ligand is selected among: testosterone, dihydrotestosterone, progesterone, medroxyprogesterone acetate, cyproterone acetate, mifepristone, dehydroepiandrosterone, flutamide; and c) glucocorticoid receptor, then the known ligand is selected among: dexamethasone, medroxyprogesterone acetate, cortivazol, deoxycorticosterone, mifepristone, fluticasone propionate, dexamethasone; and d) Peroxisome proliferators-activated receptors (PPARs), then the known ligand is selected among the glitazones; and e) Liver X Receptor alpha (LXRα), then the known ligand is selected among T1317; and f) Retinoic acid receptor (RAR), then the known ligand is selected among all-trans retinoic acid, 9-cis-retinoic acid; and g) Retinoid X receptor (RXR), then the known protein ligand is selected among all- trans retinoic acid, 9-cis-retinoic acid.

16. The method according to claim 1, wherein the members of said library of peptides are composed of less than 50 amino acids.

17. The method according to claim 1 wherein said target protein is RNA polymerase 5B.

18. The method according to claim 1, wherein said conformation-sensitive peptide selected in step C) has the ability to select agonists, antagonists and compounds other than agonists and antagonists.

19. The method according to claim 1, wherein said conformation-sensitive peptide is selected in step C) for its ability to detect conformational changes resulting from the interaction of the target protein with agonist compounds.

20. The method according to claim 1, wherein said conformation-sensitive peptide is selected in step C) for its ability to detect conformational changes resulting from the interaction of the target protein with antagonist compounds.

21. The method according to claim 1, wherein said conformation-sensitive peptide is selected in step C) for its ability to detect conformational changes resulting from the interaction of the target protein with agonists and antagonist compounds.

22. The method of claim 15, wherein the glitazone is troglitazone.

* * * * *

SEQUENCE LISTING

```
<160> NUMBER OF SEQ ID NOS: 23

<210> SEQ ID NO 1
<211> LENGTH: 13
<212> TYPE: DNA
<213> ORGANISM: Artificial sequence
<220> FEATURE:
<223> OTHER INFORMATION: Random oligonucleotide oVV1259 used to generate
      peptide libraries

<400> SEQUENCE: 1

cggccacgct gga                                                        13


<210> SEQ ID NO 2
<211> LENGTH: 18
<212> TYPE: DNA
<213> ORGANISM: Artificial sequence
<220> FEATURE:
<223> OTHER INFORMATION: Random oligonucleotide oVV1260 used to generate
      peptide libraries

<400> SEQUENCE: 2

tgaataaata ggccataa                                                   18


<210> SEQ ID NO 3
<211> LENGTH: 76
<212> TYPE: DNA
<213> ORGANISM: Artificial sequence
<220> FEATURE:
<223> OTHER INFORMATION: Random oligonucleotide oVV1261 used to generate
      peptide libraries
<220> FEATURE:
<221> NAME/KEY: misc_feature
<222> LOCATION: (16)..(16)
<223> OTHER INFORMATION: v is a, g, or c
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: v is a, g, or c
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: v is a, g, or c
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: v is a, g, or c
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: v is a, g, or c
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
```

-continued

<223> OTHER INFORMATION: v is a, g, or c
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: v is a, g, or c
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (37)..(37)
<223> OTHER INFORMATION: v is a, g, or c
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (40)..(40)
<223> OTHER INFORMATION: v is a, g, or c
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (43)..(43)
<223> OTHER INFORMATION: v is a, g, or c
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (46)..(46)
<223> OTHER INFORMATION: v is a, g, or c
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (49)..(49)
<223> OTHER INFORMATION: v is a, g, or c
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (52)..(52)
<223> OTHER INFORMATION: v is a, g, or c
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (55)..(55)
<223> OTHER INFORMATION: v is a, g, or c
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (58)..(58)
<223> OTHER INFORMATION: v is a, g, or c
<220> FEATURE:
<221> NAME/KEY: misc_feature
<222> LOCATION: (59)..(60)
<223> OTHER INFORMATION: n is a, c, g, or t

<400> SEQUENCE: 3

-continued tggcctattt attcavnnvn nvnnvnnvnn vnnvnnvnnv nnvnnvnnvn nvnnvnnvnn 60
tccagcgtgg ccgcct 76

<210> SEQ ID NO 4
<211> LENGTH: 46
<212> TYPE: DNA
<213> ORGANISM: Artificial sequence
<220> FEATURE:
<223> OTHER INFORMATION: Random oligonucleotide oVV1262 used to generate peptide libraries
<220> FEATURE:
<221> NAME/KEY: misc_feature
<222> LOCATION: (16)..(16)
<223> OTHER INFORMATION: v is a, g, or c
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: v is a, g, or c
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: v is a, g, or c
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: v is a, g, or c
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: v is a, g, or c
<220> FEATURE:
<221> NAME/KEY: misc_feature
<222> LOCATION: (29)..(30)
<223> OTHER INFORMATION: n is a, c, g, or t

<400> SEQUENCE: 4
tggcctattt attcavnnvn nvnnvnnvnn tccagcgtgg ccgcct 46

<210> SEQ ID NO 5
<211> LENGTH: 1779
<212> TYPE: DNA
<213> ORGANISM: Hepatitis C virus (HCV)
<220> FEATURE:
<223> OTHER INFORMATION: Full length NS5B 1b gene from HCV

<400> SEQUENCE: 5
atgtcaatgt cctacacatg gacaggtgcc ttgatcacgc catgcgctgc ggaggagagc 60
aagttgccca tcaatccgtt gagcaactct ttgctgcgtc accacagtat ggtctactcc 120
acaacatctc gcagcgcaag tctgcggcag aagaaggtaa cctttgacag aatgcaagtc 180
ctggacgacc actaccggga cgtgctcaag gagatgaagg cgaaggcgtc cacagttaag 240
gctaggcttc tatctataga ggaggcctgc aaactgacgc ccccacattc ggccaaatcc 300
aaatttggct acggggcgaa ggacgtccgg agcctatcca gcagggccgt caaccacatc 360

-continued

```
cgctccgtgt gggaggactt gctggaagac actgaaacac caattgatac caccatcatg     420

gcaaaaaatg aggttttctg cgtccaacca gagaaaggag gccgcaagcc agctcgcctt     480

atcgtattcc cagacctggg ggtacgtgta tgcgagaaga tggcccttta cgacgtggtc     540

tccacccttc ctcaggccgt gatgggcccc tcatacggat tccagtactc tcctgggcag     600

cgggtcgagt tcctggtgaa tacctggaaa tcaaagaaat gccctatggg cttctcatat     660

gacacccgct gctttgactc aacggtcact gagaatgaca tccgtactga ggagtcaatc     720

taccaatgtt gtgacttggc ccccgaagcc agacaggcca taaagtcgct cacagagcgg     780

ctctacatcg gggggtcccct gactaattca aaagggcaga actgcggtta tcgccggtgc    840

cgcgcgagcg gtgtgctgac gactagctgc ggcaataccc tcacatgcta cttgaaagcc     900

actgcggcct gtcgagctgc aaagctccag gactgcacga tgctcgtgaa cggagacgac     960

cttgtcgtta tctgcgaaag cgcgggaacc caggaggatg cggcgagcct acgagtcttc    1020

acggaggcta tgactaggta ctctgccccc cccggggacc cgccccaacc agaatacgac    1080

ttggagctga taacgtcatg ctcctccaat gtgtcggtcg cgcacgatgc atccggcaaa    1140

agggtgtact acctcacccg tgaccccacc acccccctcg cacgggctgc gtgggagaca    1200

gttagacaca ctccagtcaa ctcctggcta ggcaatatca tcatgtatgc gcccacccta    1260

tgggcgagga tgattctgat gactcatttc ttctctatcc ttctagctca ggagcaactt    1320

gaaaaagccc tggattgtca gatctacggg gcctgctact ccattgagcc acttgaccta    1380

cctcagatca tcgaacgact ccatggtctt agcgcatttt cactccatag ttactctcca    1440

ggtgagatca atagggtggc ttcatgcctc aggaaacttg ggtaccgccc cttgcgagtc    1500

tggagacatc gggccagaag tgtccgcgct aagctgctgt cccagggggg gagggccgcc    1560

acatgcggca aatacctctt caactgggca gtaaggacca agcttaaact cactccaatc    1620

ccggctgcgt cccagctaga cttgtccggc tggttcgttg ctggttacaa cgggggagac    1680

atatatcaca gcctgtctcg tgcccgaccc cgttggttca tgttgtgcct actcctactt    1740

tctgtagggg taggcatcta cctgctcccc aaccggtaa                           1779
```

<210> SEQ ID NO 6
<211> LENGTH: 34
<212> TYPE: DNA
<213> ORGANISM: Artificial sequence
<220> FEATURE:
<223> OTHER INFORMATION: Forward primer used as templates to amplify HCV NS5B full length and HCV NS5B ? 21

<400> SEQUENCE: 6

```
tatctcgagt caatgtccta cacatggaca ggtg                                  34
```

<210> SEQ ID NO 7
<211> LENGTH: 30
<212> TYPE: DNA
<213> ORGANISM: Artificial sequence
<220> FEATURE:
<223> OTHER INFORMATION: Reverse primer used as templates to amplify HCV NS5B ? 21

<400> SEQUENCE: 7

```
agatctgcag ttaacggggt cgggcacgag                                       30
```

<210> SEQ ID NO 8
<211> LENGTH: 28
<212> TYPE: DNA

```
<213> ORGANISM: Artificial sequence
<220> FEATURE:
<223> OTHER INFORMATION: Reverse primer used as templates to amplify
      NS5B full length

<400> SEQUENCE: 8

tatggatcct taccggttgg ggagcagg                                        28


<210> SEQ ID NO 9
<211> LENGTH: 40
<212> TYPE: DNA
<213> ORGANISM: Artificial sequence
<220> FEATURE:
<223> OTHER INFORMATION: Forward primer used as templates to amplify the
      mutant NS5B L30S

<400> SEQUENCE: 9

aatccgttga gcaactcttc gctgcgtcac caacagtatg                           40


<210> SEQ ID NO 10
<211> LENGTH: 37
<212> TYPE: DNA
<213> ORGANISM: Artificial sequence
<220> FEATURE:
<223> OTHER INFORMATION: Reverse primer used as templates to amplify the
      mutant NS5B L30S

<400> SEQUENCE: 10

catactgtgg tgacgcagcg aagagttgct caacgga                              37


<210> SEQ ID NO 11
<211> LENGTH: 34
<212> TYPE: DNA
<213> ORGANISM: Artificial sequence
<220> FEATURE:
<223> OTHER INFORMATION: Forward primer used as templates to amplify
      neuraminidase

<400> SEQUENCE: 11

ccagaattcc attcaattca attcaaactg gaag                                 34


<210> SEQ ID NO 12
<211> LENGTH: 30
<212> TYPE: DNA
<213> ORGANISM: Artificial sequence
<220> FEATURE:
<223> OTHER INFORMATION: Reverse primer used as templates to amplify
      neuraminidase

<400> SEQUENCE: 12

atactcgagc tacttgtcaa tggtgaatgg                                      30


<210> SEQ ID NO 13
<211> LENGTH: 30
<212> TYPE: DNA
<213> ORGANISM: Artificial sequence
<220> FEATURE:
<223> OTHER INFORMATION: Forward primer used as templates to amplify HIV
      p66

<400> SEQUENCE: 13

ccagaattca ttagccctat tgagactgta                                      30


<210> SEQ ID NO 14
<211> LENGTH: 51
<212> TYPE: DNA
<213> ORGANISM: Artificial sequence
```

-continued

<220> FEATURE:
<223> OTHER INFORMATION: Forward primer used as templates to amplify HIV
p66

<400> SEQUENCE: 14
ccagaattcg cagctgctgc agctgcaccc attagcccta ttgagactgt a 51

<210> SEQ ID NO 15
<211> LENGTH: 33
<212> TYPE: DNA
<213> ORGANISM: Artificial sequence
<220> FEATURE:
<223> OTHER INFORMATION: Forward primer used as templates to amplify HIV
p66

<400> SEQUENCE: 15
ccagaattcc ccattagccc tattgagact gta 33

<210> SEQ ID NO 16
<211> LENGTH: 33
<212> TYPE: DNA
<213> ORGANISM: Artificial sequence
<220> FEATURE:
<223> OTHER INFORMATION: Reverse primer used as templates to amplify HIV
p66

<400> SEQUENCE: 16
atactcgagt tatagtactt tcctgattcc agc 33

<210> SEQ ID NO 17
<211> LENGTH: 15
<212> TYPE: PRT
<213> ORGANISM: Artificial sequence
<220> FEATURE:
<223> OTHER INFORMATION: ERa 3D-screen peptide 5-21

<400> SEQUENCE: 17

Ser Cys Cys Thr Gln His Val Cys Tyr Arg Pro Arg Ala Tyr Arg
1 5 10 15

<210> SEQ ID NO 18
<211> LENGTH: 15
<212> TYPE: PRT
<213> ORGANISM: Artificial sequence
<220> FEATURE:
<223> OTHER INFORMATION: ERa 3D-screen peptide 9-23

<400> SEQUENCE: 18

Ser Ile Thr Thr Leu Phe Tyr His Ala Met Phe Gly Phe Val Pro
1 5 10 15

<210> SEQ ID NO 19
<211> LENGTH: 18
<212> TYPE: PRT
<213> ORGANISM: Artificial sequence
<220> FEATURE:
<223> OTHER INFORMATION: ERa 3D-screen peptide 30-2

<400> SEQUENCE: 19

Phe Cys Thr Pro Ile Arg Met Phe Tyr Arg Ala Pro Leu Trp Asp Leu
1 5 10 15

Asn Lys

<210> SEQ ID NO 20
<211> LENGTH: 15
<212> TYPE: PRT

-continued

```
<213> ORGANISM: Artificial sequence
<220> FEATURE:
<223> OTHER INFORMATION: RARa 3D-screen peptide I-B8

<400> SEQUENCE: 20

Met Pro Ala Asp Ile Leu Phe Ala Asn Pro Gln Cys Arg Ile Asn
1               5                   10                  15


<210> SEQ ID NO 21
<211> LENGTH: 15
<212> TYPE: PRT
<213> ORGANISM: Artificial sequence
<220> FEATURE:
<223> OTHER INFORMATION: RARa 3D-screen peptide I-C8

<400> SEQUENCE: 21

Ala Pro Phe Pro Val Val Tyr Trp Ser Asp Trp Cys Asn Gln Gln
1               5                   10                  15


<210> SEQ ID NO 22
<211> LENGTH: 18
<212> TYPE: PRT
<213> ORGANISM: Artificial sequence
<220> FEATURE:
<223> OTHER INFORMATION: RARa 3D-screen peptide III-D2

<400> SEQUENCE: 22

Trp Val Val Tyr Ala Ser Leu Cys Phe Lys Ala Cys Tyr Phe Gly Leu
1               5                   10                  15

Asn Lys


<210> SEQ ID NO 23
<211> LENGTH: 20
<212> TYPE: PRT
<213> ORGANISM: Artificial sequence
<220> FEATURE:
<223> OTHER INFORMATION: RARa 3D-screen peptide II-F8

<400> SEQUENCE: 23

Ala Thr Leu Glu Trp Arg Leu Phe Thr Arg Phe Ile Thr Trp Gly Leu
1               5                   10                  15

Ile Pro Leu Glu
            20
```